United States Patent [19]

Horii et al.

[11] Patent Number: 4,824,943

[45] Date of Patent: Apr. 25, 1989

[54] INOSOSE DERIVATIVES AND PRODUCTION THEREOF

[75] Inventors: Satoshi Horii; Hiroshi Fukase, both of Osaka, Japan

[73] Assignee: Takeda Chemical Industries, Ltd., Japan

[21] Appl. No.: 21,745

[22] Filed: Mar. 4, 1987

[30] Foreign Application Priority Data

Mar. 5, 1986 [JP] Japan ................................. 61-47941
May 21, 1986 [JP] Japan ............................... 61-116672

[51] Int. Cl.⁴ ........................ C07H 1/00; C07H 3/00; C08B 37/00; C07G 3/00
[52] U.S. Cl. .................................. 536/1.1; 536/18.5; 536/55.3; 536/124; 536/13.6
[58] Field of Search ...................... 536/13.6, 1.1, 18.5, 536/55.3, 124

[56] References Cited

U.S. PATENT DOCUMENTS 4,387,219  6/1983  Yamamoto et al. ............... 536/13.6
4,412,068  10/1983  Rosi .................................... 536/13.6
4,446,319  5/1984  Horii et al. ........................... 544/92
4,526,784  7/1985  Heiker et al. ....................... 536/18.5

FOREIGN PATENT DOCUMENTS 58-203999  11/1983  Japan .................................. 536/124
58-213794  12/1983  Japan .................................. 536/124

OTHER PUBLICATIONS

Cantrell et al.; J. Org. Chem. vol. 42 (22):3562-3567 (1977).
Riordan et al.; J. Carbohydrate Chemistry (2(2):201-205 (1983).
Noller; Ed. *Chemistry of Organic Compounds* pp. 775-6 (1957).
Morrison and Boyd; Eds. *Organic Chemistry* 3rd edition (1977) pp. 714-7155; 740-741.
Carbohydrate Research, vol. 140, pp. 185-200 (1985), Horii et al.
Bull. Chem. Soc. Jpn., vol. 56, pp. 1161-1170 (1983), Toyokuni et al.
J. Org. Chem., vol. 48, pp. 1203-1207 (1983). Ogawa et al.
Ann. Chem., 1981, pp. 2180-2203 Abstract and Figures only Frank et al.
Chem. Lett., pp. 1581-1582 (1985) Ogawa et al.

*Primary Examiner*—Ronald W. Griffin
*Assistant Examiner*—Nancy S. Carson
*Attorney, Agent, or Firm*—Wegner & Bretschneider

[57] ABSTRACT

The novel inosose derivatives

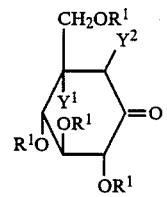

wherein $Y^1$ stands for hydroxyl group and $Y^2$ stands for hydrogen atom, or $Y^1$ and $Y^2$ are joined to form a bond between carbon and carbon atoms, and $R^1$ and is a protective group for hydroxyl group, are useful as a starting material for producing valienamine, valiolamine and their N-substituted derivatives.

7 Claims, No Drawings

INOSOSE DERIVATIVES AND PRODUCTION THEREOF

Valienamine, valiolamine and their N-substituted derivatives [J. Antibiot., 35, pp. 1624–1626 (1982); J. Antibiot., 37, pp. 1301–1307 (1984); Carbohydr. Res., 140, pp. 180–200 (1985); J. Med. Chem., 29, pp. 1038–1046 (1986)] have an inhibitory activity against α-glucosidase and are useful as prophylactic or therapeutic agents of hyperglycemic symptoms in man and other animals and various disorders caused by hyperglycemia such as diabetes, obesity, hyperlipemia, etc. The novel inosose derivative

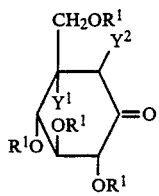 [I]

wherein $Y^1$ stands for hydroxyl group and $Y^2$ stands for hydrogen atom, or $Y^1$ and $Y^2$ are joined to form a bond between carbon and carbon atoms, and $R^1$ is a protective group for a hydroxyl group, is an important compound as starting materials for producing valienamine, valiolamine and their N-substituted derivatives.

The present inventors previously found that valienamine and valiolamine can be isolated from a culture broth of Streptomyces hygroscopicus subsp. limoneus [J. Antibiot. 37, pp. 1301–1307 (1984)]; valienamine can be prepared by subjecting validamycins or validoxylamines to microbiological degradation [Toku-Kai Sho (Japanese patent application Laid-Open No.) 57-54593 and 58-1524961]; and valiolamine can be synthesized from valienamine [Carbohydr. Res., 140 pp. 180–200 (1985); EP No. 63,950 (1982); U.S. Pat. No. 4,446,319, (1984)].

In addition, the following methods of preparing DL-valienamine and DL-valiolamine by chemical synthesis were reported; the method of preparing DL-valienamine via DL-1,2,3-tri-O-acetyl-(1,3/2,4,6)-4-bromo-6-bromomethyl-1,2,3-cyclohexanetriol as the intermediate [T. Toyokuni et al. Bull. Chem. Soc. Jpn., 56, pp. 1161–1170 (1983)]; the method of preparing DL-valienamine via DL-2,3-di-O-acetyl-1,7-O-benzylidene-(1,3,4/2,5,6)-4-azido-6-(hydroxymethyl)-1,2,3,5-cyclohexanetetrol as the intermediate [S. Ogawa et al. J. Org. Chem., 48, pp. 1203–1207 (1983)]; the method of preparing DL-penta-N,O-acetylvaliolamine via DL-1,2,3-tri-O-acetyl-(1,3/2,4)-4-bromo-6-methylene-1,2,3-cyclohexanetriol as the intermediate [S. Ogawa et al. Chem. Lett., pp. 1581–1582 (1985)]. However, the processes of resolution of the DL mixtures have not yet been established in these methods.

As a method of preparing enantiomerically pure natural-type valienamine by chemical synthesis, the method from L-(−)-quebrachitol was reported [H. Paulsen, F. R. Heiker, Justus Liebigs Ann. Chem. 1981, pp. 2180–2203], but this method comprises a number of steps, which is not necessarily suitable for industrial production of valienamine. Besides, the method of synthesizing N-substituted valienamine derivatives from D-glucose via 1D-(1,3,6/2)-4-benzoyloxymethyl-6-bromo-1,2,3-tri-O-benzyl-4-cyclohexene-1,2,3-triol and its 1D-(1,3/2,6)-isomers [N. Sakairi, H. Kuzuhara, Tetrahedron Lett., 23, pp. 5327–5330 (1982)] was also reported.

However, these above-mentioned total chemical syntheses of valienamine and valiolamine have such drawbacks as poor stereospecific processes, difficulties in availability of materials or comprising a number of reaction steps, and these methods are hardly considered industrially suitable.

A direct fermentation method of valienamine and valiolamine, namely, a method of isolating from the fermentation broth of Streptomyces hygroscopicus subsp. limoneus, is a most convenient and simple one, but, this method is not satisfactory yet at the present state in respect to the yield as an industrial method.

The method of preparing valienamine by microbiological degradation of validamycins, especially validamycin A is most excellent as an industrial method. However, this method has such a drawback as a part of constituents of validamycin A is utilizable for the purpose of preparing valienamine (the molecular weight of valienamine is about 1/2.7 relative to validamycin A), which makes the resultant valienamine comparatively expensive.

On the other hand, the present inventors found out methods of preparing N-substituted derivatives of valienamine and valiolamine by subjecting the amino group of valienamine and valiolamine to reductive alkylation with aldehydes or ketones, or by allowing the amino group of valienamine and valiolamine to react with an oxirane derivative or a halogen derivative [J. Antibiotics, 35, pp. 1624–1626 (1982); J. Med. Chem., 29, pp. 1038–1046 (1986); EP 56194 (1982) and 89812 (1983)], and valiolamine has been exclusively employed as the material for preparing N-substituted valiolamine derivatives so far. Circumstances being such, more advantageous methods for synthesizing valienamine, valiolamine and N-substituted valiolamine derivatives have been desired.

The present inventors expected that, if an inosose derivative could be used as the material for constructing the valiolamine moiety of N-substituted valiolamine derivatives, it would be possible to employ a primary amine having the corresponding structure as the material for constructing the N-substituent moiety, and when this primary amine is available more advantageously than the corresponding aldehydes, ketones, oxiranes and halides, the end product would be prepared more advantageously by this method than the method in which valiolamine is employed as the material.

Thus, the present invention relates to an inosose derivative of the formula

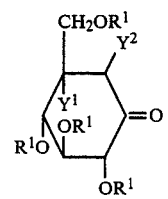 [I]

wherein $Y^1$ stands for hydroxyl group and $Y^2$ stands for hydrogen atom, or $Y^1$ and $Y^2$ are joined to form a bond between carbon and carbon atoms, and $R^1$ is a protective group for a hydroxyl group.

The present inventors have conducted diligent investigation for solving the aforementioned problems and have succeeded in preparing novel inosose derivatives representable by the general formula

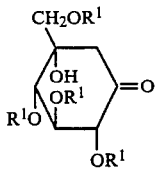 [I']

[wherein R$^1$ stands for a protective group for a hydroxyl group] by using, as the material, sedoheptulosan (2,7-anhydro-β-D-altro-2-heptulopyranose), which is a 2,7-anhydro-sugar of sedoheptulose (D-altro-2-heptulose), then have succeeded in preparing pseudo-amino sugars or a derivative thereof representable by the general formula

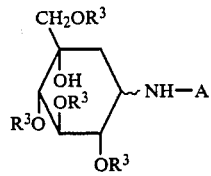 [III]

[wherein R$^3$ stands for a hydrogen atom or a protective group for a hydroxyl group, A stands for an amine residue or hydrogen atom, and the wavy bond ∼ shows a R- or S-configurational bond], by allowing a compound [I'] to react with a primary amine or hydroxylamine representable by the general formula R$^2$-NH$_2$ [II] [wherein R$^2$ stands for an amine residue or hydroxyl group], and then subjecting the resultant product to reduction, followed by, when desired, deprotection reaction.

The present inventors have further conducted diligent investigation for solving the aforementioned problems and have succeeded in preparing novel compounds representable by the general formula

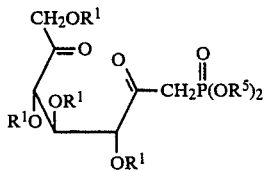 [VIII]

[wherein R$^1$ stands for a protective group for a hydroxyl group, and R$^5$ stands for a hydrocarbon residue] by employing as the starting material readily available and less expensive D-glucose or D-glucono-1,5-lactone (D-gluconic acid δ-lactone) which can be easily prepared from D-glucose, and then have succeeded in preparing novel unsaturated inosose derivatives representable by the general formula

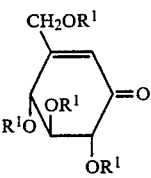 [I'']

[wherein R$^1$ stands for a protective group for a hydroxyl group], which can be an important intermediate for the synthesis of valienamine, by subjecting the compound [VIII] to treatment with a base.

In the above general formula [II], R$^2$ stands for an amine residue or hydroxyl group, and the typical amine residues are cyclic or acyclic hydrocarbon residues of 1-7 carbon atoms optionally having optionally protected hydroxyl groups and/or optionally substituted phenyl groups.

Primary amines representable by the general formula; R$^2$-NH$_2$ are practically exemplified by acyclic alkyl amines optionally having hydroxyl group and/or optionally substituted phenyl group, such as ethanolamine, 3-amino-1-propanol, 2-amino-1-propanol, 2-amino-1,3-propanediol, 1-amino-2-propanol, 2-amino-3-hydroxy-1-butanol, tris(hydroxymethyl)aminomethane, 2-amino-2-methyl-1,3-propanediol, 2-amino-2-methyl-1-propanol, 2-amino-3-methyl-1-butanol, 3-amino-1,2-propanediol, 4-amino-1,2-butanediol, 2-amino-1-butanol, 2-amino-1,4-butanediol, 2-amino-1,5-pentanediol, 5-amino-1-pentanol, 6-amino-1-hexanol, methylamine, ethyl-amine, propylamine, butylamine, benzylamine, phenethylamine, aminodiphenylmethane, 2-amino-1-phenylethanol, 2-amino-2-phenylethanol, 2-amino-3-phenyl-1-propanol, 2-amino-3-hydroxy-3-phenyl-1-propanol, 2-amino-3-(4-hydroxyphenyl)-1-propanol, β-amino-α-methylphenethylalcohol, etc.; aminodeoxy-alditols, such as 1-amino-1-deoxy-D-glucitol, 2-amino-2-deoxy-D-glucitol, 1-amino-1-deoxy-D-mannitol, 2-amino-2-deoxy-D-galactitol, 1-amino-1-deoxy-D-ribitol, 4-amino-4-deoxy-D-erythritol, etc.; cyclic alkylamines optionally substituted with hydroxyl group and/or phenyl group, such as trans-2-aminocyclohexan-1-ol, trans-3-aminocyclohexan-1-ol, cis-3-aminocyclohexan-1-ol, trans-2-amino-1-phenylcyclohexan-1-ol, cis-2-amino-1-phenylcyclohexan-1-ol, cyclohexylamine, cyclopentylamine, 1-amino-1-cyclopentane methanol, 2-aminocyclopentanol, etc.; inosamines such as myo-inosamine-1, myo-inosamine-2, myo-inosamine-4, neo-inosamine-2, epiinosamine-2, muco-inosamine-3, scyllo-inosamine, etc.; C-(aminomethyl-)inositols such as 2-(aminomethyl)myoinositol, etc.; diaminocyclitols such as streptamine, deoxystreptamine, fortamine, sporamine, istamine, etc.; pseudo-amino sugars such as valienamine, validamine, hydroxyvalidamine, valiolamine, 2-hydroxy-4-(hydroxymethyl)cyclopentylamine, etc. Hydroxyl groups of the above-mentioned compounds may optionally be protected. In the above-mentioned formulae [II] and [III], the amine residue represented by A is practically exemplified by all of the amine residues (i.e. R$^2$) of amines set forth as primary amines representable by the above R$^2$-NH$_2$.

As the protective group for hydroxyl represented by R$^1$ and R$^3$ in the above formulae [I], [I'] and [III], use is made of protective groups established in the chemistry of sugars, such as acyl type protective groups, ether type protective groups, acetal type protective groups, ketal type protective groups or orthoester type protective groups.

The acyl type protective groups include e.g. alkanoyl group of 1 to 5 carbon atoms which may be substituted by halogen, lower alkoxyl of 1 to 5 carbon atoms or phenoxy optionally bearing halogen; benzoyl groups which may be substituted by lower alkyl of 1 to 5 carbon atoms which may be substituted by nitro, phenyl or halogen or lower alkyloxycarbonyl of 2 to 6 carbon atoms; alkoxycarbonyl of 2 to 6 carbon atoms which may be substituted by halogen; alkenyloxycarbonyl of 3 to 5 carbon atoms; benzyloxycarbonyl groups which may be substituted by lower alkoxyl of 1 to 5 carbon atoms or nitro; phenoxycarbonyl substituted by nitro; etc.

As the halogen, use is made of fluorine, chlorine, bromine or iodine; as the alkyl of 1–5 carbon atoms, use is made of, for example, methyl, ethyl, propyl, isopropyl, butyl, isobutyl, sec.-butyl, tert-butyl, pentyl, isopentyl, neopentyl etc.; as the alkanoyl of 1 to 5 carbon atoms, use is made of, for example, formyl, acetyl, propionyl, butyl, isobutyryl, isovaleryl, pivaloyl etc.; as the alkoxyl of 1 to 5 carbon atoms, use is made of, for example, methoxyl, ethoxyl, propoxyl, pentyloxy, vinyloxy, allyoxy, etc. which may be substituted by halogen.

As the alkenyl of 2–4 carbon atoms in the above alkenyloxycarbonyl of 3–5 carbon atoms, use is made of, for example, vinyl, allyl, isopropenyl, 1-propenyl, 1-butenyl, 2-butenyl, 3-butenyl, etc.

More concretely, the examples of acyl type protective groups are formyl, acetyl, chloroacetyl, dichloroacetyl, trichloroacetyl, trifluoroacetyl, methoxyacetyl, triphenylmethoxyacetyl, phenoxyacetyl, p-chlorophenoxyacetyl, propionyl, isopropionyl, 3-phenylpropionyl, isobutyryl, pivaloyl; benzoyl, p-nitrobenzoyl, p-phenylbenzoyl, o-(dibromomethyl)benzoyl, o-(methoxycarbonyl)benzoyl, 2,4,6-trimethylbenzoyl; methoxycarbonyl, ethoxycarbonyl, 2,2,2-trichloroethoxycarbonyl, isobutyloxycarbonyl; vinyloxycarbonyl, allyloxycarbonyl; benzyloxycarbonyl, p-methoxybenzyloxycarbonyl, 3,4-dimethoxybenzyloxycarbonyl, p-nitrobenzyloxycarbonyl; p-nitrophenoxycarbonyl, etc.

The ether type protective groups include, for example, lower alkyl groups of 1–5 carbon atoms which may be substituted by halogen, lower alkoxyl of 1–5 carbon atoms, benzyloxy or phenyl; alkenyl groups of 2–4 carbon atoms; trisubstituted silyl groups substituted by lower alkyl of 1–5 carbon atoms, phenyl, benzyl, etc.; benzyl group which may be substituted by lower alkoxyl of 1–5 carbon atoms or nitro; tetrahydropyranyl group or tetrahydrofuranyl group, which may be substituted by lower alkoxy of 1–5 carbon atoms or halogen.

As the above-mentioned halogen, lower alkyl groups of 1–5 carbon atoms, lower alkoxyl groups of 1–5 carbon atoms and alkenyl groups of 2–4 carbon atoms, use is made of ones similar to those used in the case of the acyl type protective groups.

More concretely, the other type protective groups are methyl, methoxymethyl, benzyloxymethyl, tert-butoxymethyl, 2-methoxyethoxymethyl, 2,2,2-trichloromethoxymethyl, ethyl, 1-ethoxyethyl, 1-methyl-1-methoxyethyl, 2,2,2-trichloroethyl, propyl, isopropyl, butyl, isobutyl, sec-butyl, tert-butyl, ethoxyethyl, triphenylmethyl, p-methoxyphenyldiphenylmethyl; allyl; trimethylsilyl, tert-butyldimethylsilyl, tert-butyldiphenylsilyl; benzyl, p-methoxybenzyl, p-nitrobenzyl, p-chlorobenzyl; tetrahydropyranyl, 3-bromotetrahydropyranyl, 4-methoxytetrahydropyranyl, tetrahydrofuranyl, etc.

The acetal type, ketal type and orthoester type protective groups are preferably those of 1 to 10 carbon atoms. Specific examples of them are methylene, ethylidene, 1-tert-butylethylidene, 1-phenylethylidene, 2,2,2-trichloroethylidene; isopropylidene, butylidene, cyclopentylidene, cyclohexylidene, cycloheptylidene; benzylidene, p-methoxybenzylidene, 2,4-bromomethoxybenzylidene, p-dimethylaminobenzylidene, o-nitrobenzylidene; methoxymethylene, ethoxymethylene, dimethoxymethylene, 1-methoxyethylidene, 1,2-dimethoxyethylidene, etc.

Further, stannoxane type protecting groups such as dibutylstannyl, tributylstannyl, cyclic carbonate type protecting groups, cyclic boronate type protecting groups, etc. can be used likewise.

Types of the protective groups for the hydroxyl group represented by $R^1$ and $R^3$ may be the same or two or more different ones. Further, as in the cases of cyclic acetal, cyclic ketal, cyclic orthoester, cyclic carbonate, cyclic boronate and stannoxane type protective groups, two hydroxyl groups may be protected with a one protective group.

It has been known that sedoheptulose, a starting material of the compound [I'], is accumulated in a culture broth of microorganisms such as a certain species of bacteria, actimomycetes, etc. [cf. e.g. J. Biochem. (Tokyo), 54, pp. 107–108 (1963); Japanese patent application publication No. 5240/1982], and sedoheptulose can be purified and isolated from the culture broth of these microorganisms. Further, by heating sedoheptulose in a dilute mineral acid e.g. dilute sulfuric acid, sedoheptulosan (2,7-anhydrosedheptulose) can be isolated as crystals. Preparation of D-idoheptulosan(2,7-anhydro-β-D-ido-2-heptulopyranose) from sedoheptulosan can be conducted by, for example, the reaction steps as shown in Scheme 1:

(i) protecting the hydroxyl groups at 4- and 5-position of sedoheptulosan with a protecting group e.g. isopropylidene group, (ii) protecting the hydroxyl groups at 1- and 3-position with e.g. benzoyl group (Bz), (iii) removing the protecting groups for hydroxyl groups at 4- and 5-position, (iv) protecting the hydroxyl group at 4-position with a protecting group e.g. benzoyl group, (v) organosulfonylating, for example, imidazolylsulfonylating the hydroxyl group at 5-position, (vi) inverting configuration of the hydroxyl group at 5-position by reacting with acyloxy anion e.g. benzoyloxy anion, and (vii) removing the protecting group for hydroxyl group, when necessary.

Scheme 1

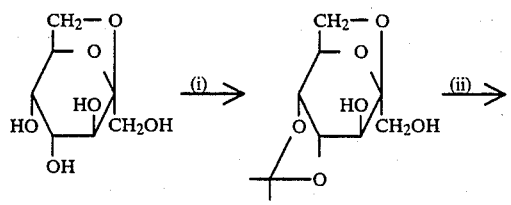

-continued
Scheme 1

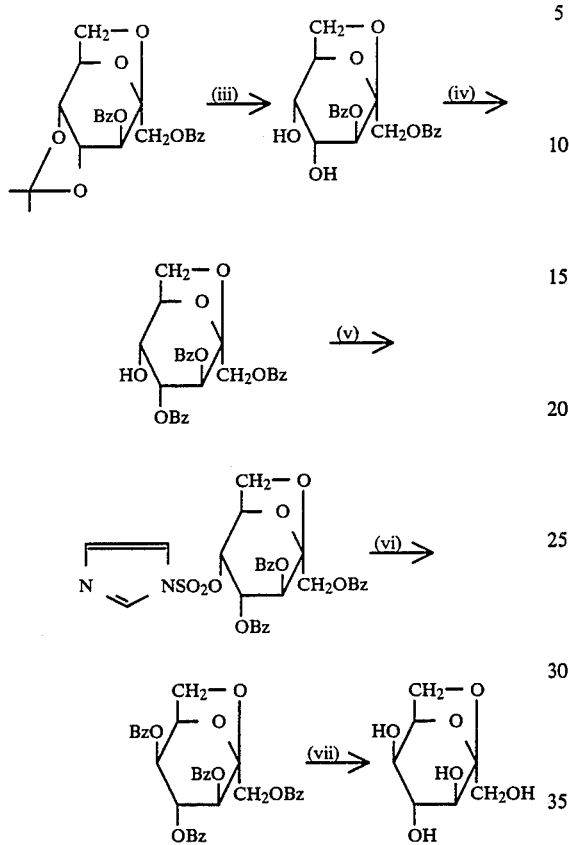

Scheme 2

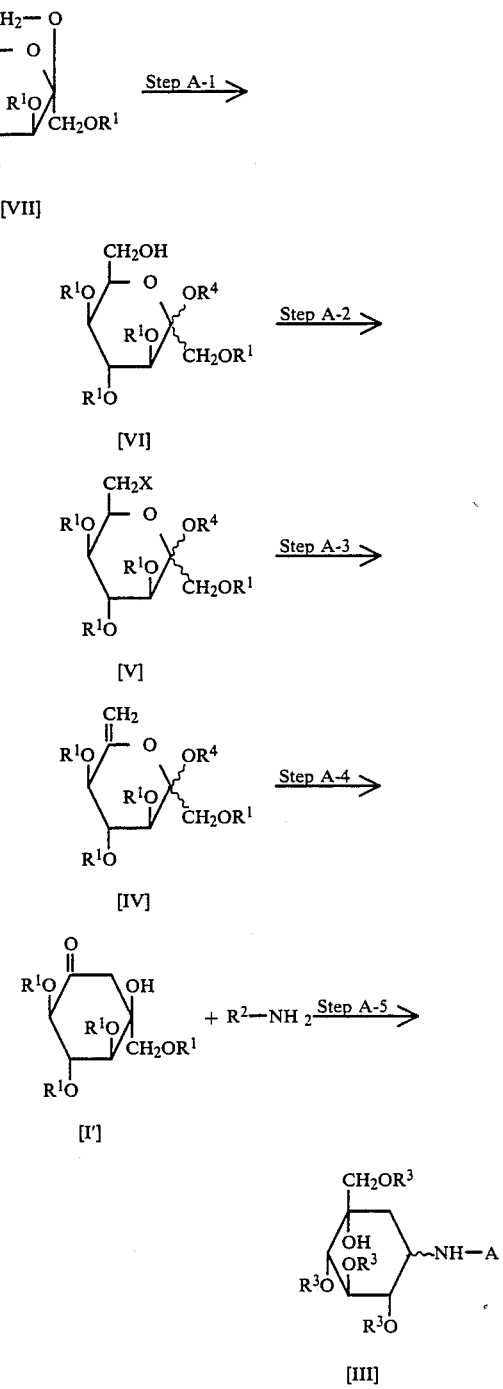

Methods of preparing D-idoheptulosan(2,7-anhydro-β-D-ido-2-heptulopyranose) and its 1,3,4,5-tetra-O-acetyl derivatives via 2,7-anhydro-β-D-arabino-2,5-heptodiulopyranose from sedoheptulosan are reported by K. Heyns et al. [Chem. Ber., 108, pp. 3611–3618 (1975)], and a method of preparing D-idoheptulose and 2,7-anhydro-β-D-idoheptulopyronose by subjecting D-gluco-D-ido-heptitol to microbiological oxidation are reported by J. W. Pratt [J. Am. Chem. Soc., 74, pp. 2210–2214 (1952)]. By resorting to these known methods, D-idoheptulosan [compound [VII] wherein $R^1$=H in Scheme 2] and D-idoheptulosan whose hydroxyl group is protected by a hydroxy protective group can be prepared as well.

Methods of preparing the compound [I'] from D-idoheptulosan [VII] [compound [VII] wherein $R^1$=protective group for hydroxyl group] are described in detail as follows. In the formulae [I'], [II] to [VII] in Scheme 2, $R^1$, $R^2$, $R^3$ and A are of the same meaning as defined above, $R^4$ stands for hydrogen for a protective group of anomeric hydroxyl group; X stands for halogen atom such as iodine, bromine, chlorine, fluorine.

Step A-1

The compound [VI] can be prepared by subjecting the 2,7-anhydro linkage of the compound [VII] to cleavage reaction. A preferable example of the protective group for a hydroxyl group represented by $R^1$ of the compound [VI] is benzoyl. For performing this cleavage reaction of the anhydro linkage, conventional methods for cleavage of an anhydro linkage of sugars [cf. for example the review articles titled "1,6-anhydro derivatives of aldohexoses" by M. Cerny and J. Stanek Jr., in Adv. Carbohyd. Chem. Biochem. 34, pp. 63–69 (1977)] are employed. The cleavage of the anhydro linkage is conducted in the presence of, for example, an acid. As suitable acids are exemplified inorganic acids such as sulfuric acid, hydrogen chloride (hydrochloric acid), hydrobromic acid (hydrogen bromide), nitric acid, perchloric acid, etc.; organic acids such as p-toluenesulfonic acid, acetic acid, acetic anhydride, trifluoroacetic acid, trifluoroacetic anhydride, etc.; Lewis acids such as boron trifluoride, boron trichloride, boron tribromide, zinc chloride, aluminium chloride, titanium tetrachloride, stannic chloride, phosphorus pentachloride, phosphorus pentabromide, phosphorus pentoxide, etc. These acids can be used singly or in admixture of two or more of them.

This cleavage reaction is usually conducted in a solvent. In this case, some solvents can be used for dual purposes of acting as solvent and reaction reagent. As the solvent can be used water, methanol, ethanol, propanol, trimethoxymethane, ethyl ether, chloroform, dichloromethane, acetone, acetic acid, trifluoroacetic acid, acetic anhydride, trifluoroacetic anhydride and any other solvent which does not exert an adverse influence on the reaction, singly or as a mixed solvent. As preferable processes can be mentioned a process comprising reaction with trimethoxymethane and zinc chloride in methanol, reaction with trifluoroacetic acid and trifluoroacetic anhydride in a trimethoxymethane solution, etc., and in these cases, compounds whose $R^4$ is methyl are obtained. The reaction temperature is not particularly limitative, and the reaction is conducted under cooling, room temperatures or under heating.

After the reaction, when necessary, removal of a protective group for a hydroxyl group containing an anomeric hydroxyl group and re-introduction thereof may be conducted.

Step A-2

The compound [V] can be prepared by subjecting the compound [VI] to halogenation. (While secondary hydroxyl groups of C-3, C-4 and C-5 are not always necessary to be protected, the primary hydroxyl group of C-1 and the anomeric hydroxyl group of C-2 are desirably protected.)

The halogenation can be conducted by resorting to conventional methods of halogenation of hydroxyl groups of sugars [cf. for example, the review articles titled "Some Approaches to the Synthesis of Halodeoxy Sugars" by S. Hanessian in Advances in Chemistry Series 74; Deoxy Sugars, pp. 159–201(1968), edited by American Chemical Society and the review articles titled ∂Deoxyhalogeno Sugars" by W. A. Szarek in Adv. Carbohydr. Chem. Biochem., 28, pp. 225–306 (1973)].

Methods of halogenation suitable for this halogenation are exemplified by a method comprising allowing phosphines such as triphenyl phosphine to react with N-halogenosuccinimide such as N-iodosuccinimide, N-bromosuccinimide, N-chlorosuccinimide, etc., preferably N-iodosuccinimide, and a method comprising activating hydroxyl group by sulfonylating with an organic sulfonyl group such as p-tolylsulfonyl, methylsulfonyl, trifluoromethanesulfonyl, imidazolylsulfonyl group, etc., followed by allowing to react with a halogenated metal MX (M stands for alkali metal such as lithium, sodium, potassium, etc., and X stands for halogen atom such as fluorine, chlorine, bromine, iodine, etc.), preferably sodium iodide.

The halogenation is conducted usually in a solvent. The solvent is exemplified by N,N-dimethylformamide, dimethylsulfoxide, pyridine, acetone, 2,4-pentanedione, 2-butanone, ethylene glycol, methanol, ethanol, glycerol, dioxane, tetrahydrofuran, chloroform, tetrachloroethane, carbon tetrachloride, benzene, etc. Besides, solvents which do not exert untoward influence upon the reaction can be employed singly or an admixture. The reaction temperature is not particularly limitative, and the reaction is conducted under cooling, room temperature or under heating.

Step A-3

The 6,7-unsaturated compound [IV] can be prepared by subjecting the 7-halogeno compound [V] to dehydrohalogenation. This elimination reaction of hydrogen halogenide can be conducted by resorting to conventional methods [cf. for example, the review articles on "Synthesis and Reactions of Unsaturated Sugars" by L. Hough described on Advances in Chemistry Series 74: Deoxy Sugars, pp. 120–140 (1968), edited by American Chemical Society]. This reaction is conducted by, preferably, allowing the compound [V] to react with anhydrous silver fluoride in pyridine.

Step A-4

For example, compound [I'] can be prepared by treating compound [IV] with mercury (II) salts such as mercury (II) chloride, mercury (II) acetate, mercury (II) trifluoroacetate, mercury (II) sulfate etc. in an aqueous organic solvent such as aqueous acetone. The reaction temperature is usually in the range of 10° C. to the refluxing temperature of the reaction solvent. The reaction time is usually in the range of 2 to 10 hours, although it depends on the reaction temperature.

Step A-5

The pseudo-amino sugar representable by the general formula [III] (wherein A stands for an amine residue, $R^3$ and the wavy bond ⁓ are of the same meaning as defined in the foregoing) can be prepared by subjecting the Schiff base obtainable by allowing the compound [I'] to react with a primary amine representable by the general formula [II] (wherein $R^2$ stands for amine residue) to reduction, followed by, when desired, subjecting the resultant to a reaction for removing the protective group.

The above-mentioned Schiff base formation reaction and reduction of the formed Schiff base can be conducted in a continuous manner in one and the same reaction vessel.

The condensation reaction of the compound [I'] and the above-mentioned primary amine [II] and the reduction of the resultant Schiff base are conducted generally in a solvent. Examples of suitable solvents are water; alcohols such as methanol, ethanol, propanol, butanol, etc.; dimethyl sulfoxide, N,N-dimethylformamide; N-methylacetamide; glymes such as methyl cellosolve dimethyl cellosolve, diethylene glycol dimethyl ether, etc.; and a mixture of these solvents. In addition, a mixture of the above-mentioned solvent and an aromatic hydrocarbon, such as benzene, toluene etc., or an ester, such as ethyl acetate etc., may be used.

The reaction temperature of the Schiff base forming reaction is not particularly limitative, and the reaction is usually conducted in the range of room temperatures to about 100° C. The reaction time varies with the reaction temperature, and usually several minutes to about 24 hours reaction is sufficient for attaining the purpose.

For carrying out the reduction of thus-formed Schiff base, are advantageously employed various metal complex hydride reducing agents, for example, alkali metal borohydride such as sodium borohydride, potassium borohydride, lithium borohydride, sodium trimethoxyborohydride, etc., alkali metal cyanoborohydride such as sodium cyanoborohydride, alkali metal aluminium hydride, etc., dialkyl amine borane such as dimethylamine borane, etc. Additionally, when alkali metal cyanoborohydride e.g. sodium cyanoborohydride is used, the reaction is conducted preferably under acid condition, for example, in the presence of hydrochloric acid, acetic acid, etc.

Reaction temperature of this reduction is not particularly limitative, and the reaction is conducted usually at room temperatures, and, depending on cases, under ice-cooling especially at the initial stage of the reaction, and also, depending on cases, under heating to about 100° C. Practically, the reaction temperature varies with the kinds of Schiff base to be reduced and reducing agents to be employed. The reaction time also varies with the reaction temperature and with the kinds of Schiff base to be reduced and reducing agents, and the reaction for several minutes to about 24 hours is enough to attain the purpose.

As the reduction of the Schiff base thus-formed, a means of catalytic reduction can also be employed. More concretely, the catalytic reduction is conducted by subjecting the Schiff base to shaking or stirring in a suitable solvent in a stream of hydrogen in the presence of a catalyst for catalytic reduction. As the catalyst, use is made of, for example, platinum black, platinum dioxide, palladium black, palladium carbon, Raney nickel, etc. As the solvent to be usually employed are mentioned, for example, water; alcohols such as methanol, ethanol, etc.; ethers such as dioxane, tetrahydrofuran, etc., N,N-dimethylformamide or a mixture of them. The reaction is conducted at room temperature under atmospheric pressure, but the reaction may be conducted under elevated pressure and by heating.

The compound [III] wherein A is a hydrogen atom can be prepared by, for example, allowing the compound [I'] to react with the compound [II] wherein $R^2$ is hydroxyl group, i.e. hydroxylamine to give an oxime, followed by subjecting the oxime to reduction. Alternatively, instead of hydroxylamine, O-substituted hydroxylamine such as O-methylhydroxylamine or O-benzylhydroxylamine is allowed to react with the compound [I'], followed by subjecting the resultant O-alkyl oximes or O-aralkyl oximes to reduction. The reduction of the hydroxyimino group of the oximes thus obtained to amino group can be conducted before or after removal of the of the protective group for hydroxyl group of the cyclitol moiety.

The reduction can be conducted by subjecting to catalytic reduction in a suitable solvent using a platinum catalyst such as platinum oxide, etc., palladium catalyst such as palladium carbon, etc., nickel catalyst such as Raney nickel, etc., rhodium catalyst such as rhodium carbon, etc. or by subjecting to reduction in a suitable solvent using an aluminium hydride compound such as lithium aluminium hydride, etc., more preferably, in an atmosphere of an inert gas such as nitrogen, argon, etc. The compound [III], wherein A is a hydrogen atom, can also be prepared starting from the compound [I'], via a compound [III], wherein the A moiety is a substituent e.g. benzyl group, p-methoxybenzyl group, 3,4-dimethoxybenzyl group or di(p-methoxyphenyl)methyl group conventionally employable as protecting groups for amino group, then by subjecting the resultant product to a conventional reaction for removing the protecting group for an amino group, exemplified by hydrogenolysis by means of catalytic reduction, reaction with metallic sodium in liquid ammonia, reaction with an acid (e.g. concentrated sulfuric acid-trifluoroacetic anhydride, acetic acid, trifluoroacetic acid, formic acid, etc.), etc.

When the compound [III] has protected hydroxyl groups, removal of the protective groups for hydroxyl groups can be conducted by resorting to a per se conventional method. For example, acetal type protective groups such as a cyclohexylidene group, isopropylidene group, benzylidene group, etc. or trityl group can be removed by subjecting them to hydrolysis with an acid such as hydrochloric acid, acetic acid, sulfonic acid type resin, etc.; acyl type protective groups such as acetyl group, benzoyl groups, etc. can be removed by subjecting them to hydrolysis with an alkali such as ammonia sodium hydroxide, barium hydroxide, sodium methoxide, etc.; and benzyl ether type protective groups such as a benzyl group, p-methoxybenzyl group, etc. can be removed by subjecting them to hydrogenolysis by means of catalytic reduction or by subjecting them to reductive cleavage with metallic sodium in liquid ammonia; etc.

A concrete description of the method of preparing the compound [I''] and the method of preparing valienamine from the compound [I''] is given below, and the schema of the production steps are shown in Scheme 3 and Sheme 4. In each of the schema, $R^1$ stands for a protecting group for hydroxyl, $R^5$ stands for a hydrocarbon residue and $R^6$ stands for an organic residue of organic sulfonyl group.

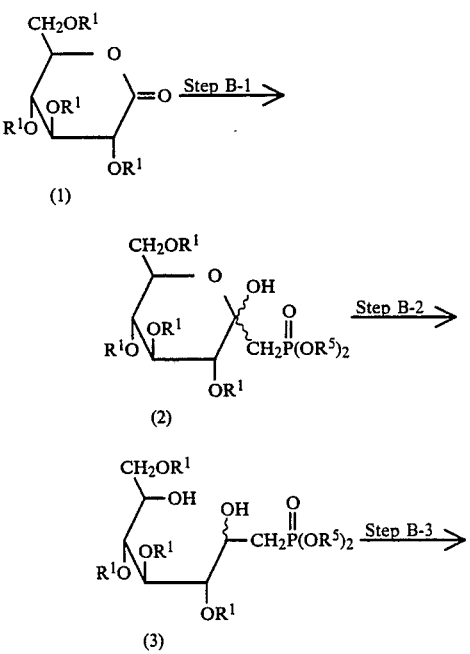

Scheme 3

-continued

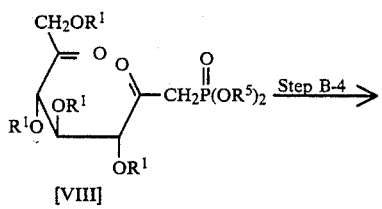

[VIII]

Scheme 4

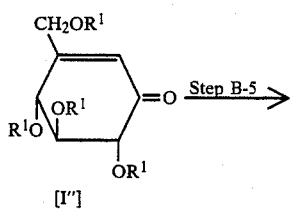

[I″]

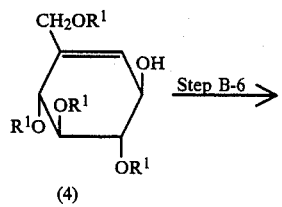

(4)

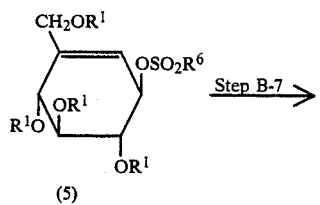

(5)

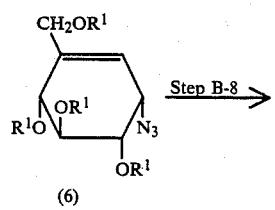

(6)

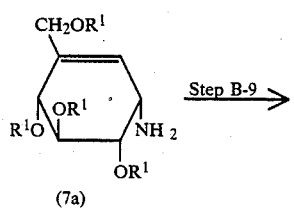

(7a)

-continued

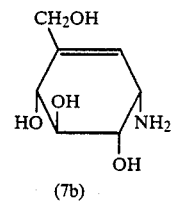

(7b)

In the general formula [I″], the general formula [VIII] and other formulae shown in Scheme 3 and 4, as the protective groups for hydroxyl group shown by $R^1$, use is advantageously made of protective groups which are employed as hydroxyl-protective group in the chemistry of sugars, for example, ether type protective groups, acetal type protective groups, ketal type protective groups, orthoester type protective groups.

In the general formula [VIII], as the hydrocarbon residues representable by $R^5$ are mentioned, for example, alkyl groups such as methyl, ethyl, propyl, isopropyl, butyl, etc., aryl groups such as phenyl, etc., aralkyl groups such as benzyl, etc., and a lower alkyl group of 1–4 carbon atoms is conveniently employed.

The compounds [I″] can be synthesized by employing a glucono-1,5-lactone derivative (1) as the starting material through the following steps B-1 to B-4, namely;

Step B-1 allowing phosphonate carbanion, which is obtainable by subjecting methyl phosphonic acid ester represented by the general formula $CH_3P(O)(OR^5)_2$ [IX] (wherein $R^5$ stands for hydrocarbon residue) to the treatment with a base, for example, n-butyllithium, to react with a glucono-1,5-lactone derivative (1) to give a 1-deoxyl-1-phosphoryl-D-gluco-2-heptulopyranose derivative (2), Step B-2 subjecting the carbonyl group forming the hemiketal of the compound (2) to reduction into hydroxyl group to thereby open the pyranose ring to give a heptitol derivative (3), Step B-3 oxidizing the hydroxyl groups at 2- and 6-position of the compound (3) into carbonyl group to give a 1-deoxy-1-phosphoryl-D-xylo-2,6-heptodiulose derivative [VIII], and Step B-4 treating the compound [VIII] with a base to give a 4L-4,6/5-trihydroxy-3-hydroxymethyl-2-cyclohexenone derivative [I″].

Valienamine and derivatives thereof can be synthesized by, for example, as shown in Schme 4, employing the compound [I″] as the starting material through the following Steps B-5 to B-9, namely;

Step B-5 reducing the carbonyl group of the compound [I″] to hydroxyl group to give an L-(1,3/2,4)-5-hydroxymethyl-5-cyclohexene-1,2,3,4-tetrol derivative (4), Step B-6 subjecting the hydroxyl group at 1-position of the compound (4) to organo-sulfonylation to give a compound (5),

Step B-7 substituting the organo-sulfonyloxy group of the compound (5) with azido group to give an azido-derivative (6),

Step B-8 and Step B-9 reducing the azido group of the compound (6) to amino group, followed by, when necessary, removing the hydroxyl-protective group to give valienamine and its derivatives.

Alternatively, in place of Step B-2 and B-3, the compound (2) is treated with a base such as sodium hydride, potassium tert-butoxide, etc. to convert the carbonyl group of hemi-ketal type into enolate type to open the pyranose ring, followed by subjecting the hydroxyl group to oxidation to synthesize the compound [VIII]. [H.-J. Altenback et al. Tetrahedron Letters, 26, pp. 6329–6332 (1985)]

The compound (7a) can also be produced by, instead of resorting to Step B-5 to B-8, subjecting the oxime (or O-alkyl oxime or aralkyl oxime) obtainable by allowing the compound [I″] to react with hydroxylamine (or O-substituted hydroxylamine such as O-methyl hydroxylamine or O-benzylhydroxylamine) to reduction. Reduction of the hydroxylimino group of oximes to amino group can be carried out in the state that the hydroxyl group at the cyclitol moiety is protected, or the reduction may be carried out after eliminating the hydroxyl group to obtain the compound (7b). The reduction can be conducted by using a metal hydride complex e.g. lithium aluminium hydride.

As specific examples of methyl phosphonic acid ester of the general formula [IX] employed in Step B-1 are mentioned a dialkyl ester of 1–4 carbon atoms e.g. dimethyl ester, diethyl ester, dipropyl ester, dibutyl ester; diaryl ester e.g. diphenyl ester; diaralkyl ester e.g. dibenzyl ester, of methylphosphoric acid. Besides, methods employing methyl diphenyl phosphine oxide in which the $(OR^5)_2$ moiety of the compound [IX] is replaced by $(C_6H_5)_2$ and methyl phosphonic acid bis(-dimethylamine) in which the $(OR^5)_2$ moiety of the compound [IX] is replaced by $[(CH_3)_2N]_2$ are also included in the category of the method employing methylphosphonic acid ester. The reaction is normally conducted at $-78°$ C. to $40°$ C., especially at the initial stage of the reaction, the reaction is conducted by cooling to about $-78°$ C., preferably in an atmosphere of an inert gas e.g. argon, nitrogen, etc. The reaction time varies depending upon the reaction temperatures and is normally in the range of 30 minutes to 3 hours.

Reagents employable for reducing a carbonyl group to a hydroxyl group in Step B-2 and B-5 are exemplified by metal hydride complexes, diborane, substituted diborane, etc., more specifically boron hydride complex such as sodium borohydride, potassium borohydride, lithium borohydride, zinc borohydride, sodium trimethoxyborohydride, potassium tri-sec-butylborohydride, lithium tri-sec-butylborohydride, sodium tri-sec-butylborohydride, potassium trisiamyl borohydride, lithium triamylborohydride, etc.; alkali metal cyanoborohydride such as sodium cyanoborohydride, tetra-n-butylammonium cyanoborohydride, etc.; alkali metal aluminium hydride such as lithium aluminium hydride, lithium trimethoxyaluminium hydride, lithium tri(tert-butoxy)aluminium hydride, etc.; alkyl borane such as 2,3-dimethyl-2-butyl borane, bis-3-methyl-2-butyl borane, diisopinocamphenyl borane, dicyclohexyl borane, 9-borabicyclo[3.3.1]nonane, NB-Enantrane, NB-Enantride, etc., alkylaminoborane such as tetramethyl ammonium borohydride, etc.; etc.

The temperatures for these reduction reactions vary depending upon the type of reducing agents, and normally in the range of from $-30°$ C. to $40°$ C., and, as the case may be, especially at the initial stage of the reaction under cooling to about $-78°$ C., and, when occasion demands, at about $80°$ C. The reaction time also varies depending upon the reaction temperature as well as the type of reducing agents, and the objective can be achieved by conducting the reaction normally in the range of several minutes to 24 hours.

In Step B-3, for preparing the heptodiulose derivative [VIII] by oxidizing the unprotected hydroxyl group of the heptitol derivative (3), the reaction condition of oxidizing the secondary hydroxyl group of sugars or polyhydric alcohol to carbonyl group is employed. For example, oxidation by using dimethyl sulfoxide and an activating reagent thereof, namely, dimethyl sulfoxide and trifluoroacetic anhydride; dimethyl sulfoxide and acetic anhdyride; dimethyl sulfoxide and phosphorus pentoxide; diemthyl sulfoxide and sulfur trioxide-pyridine complex; dimethyl-sulfoxide and oxalyl chloride; etc., is employed, and especially the oxidation by using dimethyl sulfoxide and trifluoroacetic anhydride is preferable. Alternatively, oxidation by using chromium trioxide-pyridine complex, pyridinium dichromate, ruthenium oxide (VIII), etc. may be employed.

The reaction conditions vary with the type of oxidizing agents, and as to the reaction solvent, for example, use can be made of dichloromethane, chloroform, benzene, toluene, dimethylformamide, dimethylsulfoxide, acetic anhydride, etc., singly or in admixture. The reaction is normally carried out at temperatures in the range of from $-10°$ C. to $40°$ C., and as the case may be, especially at the initial stage of the reaction, by cooling to about $-78°$ C. The reaction time is in the range of one hour to 24 hours.

The reaction for preparing the unsaturated inosose derivative [I″] in Step B-4, which comprises subjecting the phosphoryl-diketose derivative [VIII] to intramolecular ring-closure reaction by treating with a base, belongs to reactions known as intramolecular Wittig reaction or Wadsworth-Emmons reaction [cf.: W. S. Wadsworth, Jr., Organic Reaction, 24, pp. 73–253 (1977); K. B. Becker, Tetraheron, 36, pp. 1717–1745 (1980); W. S. Wadsworth, Jr., and W. D. Emmons, J. Amer. Chem. Soc. 83 pp. 1733–1738, (1961)], and methods known in connection with these methods are advantageously employed.

As the base usable for the intramolecular ring-closure reaction of the compound [VIII] into the compound [I″], use is made of, for example, alkali metal salts such as potassium carbonate, sodium carbonate, potassium hydrogencarbonate, etc.; alkali metal hydroxides such as potassium hydroxide, sodium hydroxide, etc.; alkali metal hydrides such as sodium hydride, potassium hydride, lithium hydride, etc.; alkali metal alkoxides such as sodium methoxide, sodium ethoxide, potassium-tert-butoxide, etc.; alkyl alkali metals such as butyllithium, propyllithim, etc. Among the intramolecular ring-closure reactions employing a base for converting the compound [VIII] into the compound [I″], preferable one are those employing, as the base, an alkali metal carbonate such as potassium carbonate, sodium carboante, etc. in the presence of crown ether such as 18-crown-6, dibenzo-18-crown-6, dicyclohexyl-18-crown-6, 15-crown-5, etc. [cf.: P. A. Aristoff, Synthetic Communication, 13, pp. 145–150 (1983)]. The reaction solvent varies depending upon the kind of bases then employed, and, for example, aromatic hydrocarbons such as benzene, toluene, etc., ethers such as tetrahydrofuran, ethylene glycol monoethylether, ethyl-ether, etc. are used advantageously. The reaction time also varies with the kind of bases or reaction solvents, and the reaction is conducted normally in the range of 10° C. to the boiling point of the solvent, and, as the case may be, the reaction is carried out, especially by cooling to about −78° C. at the initial stage. The reaction time varies with the reaction temperature, and it is normally in the range of 1 to 18 hours.

As method of preparing the compound (5), in Step B-6, by subjecting the unprotected hydroxyl group of the unsaturated pseudo sugar derivative (4) to organosulfonylation, is exemplified a method which comprises allowing the compound (4) to react with sulfonyl halides representable by the general formula $R^6$—$SO_2$—X [wherein X stands for a halogen such as chlorine, bromine, iodine, etc., and $R^6$ stands for a lower alkyl group; phenyl group which may optionally substituted by chlorine, bromine, iodine, a lower alkyl group, a lower alkoxy group, nitro group; benzyl group; naphthyl group and imidazolyl group] preferably, a method which comprises allowing the compound (4) to react with, for example, methanesulfonyl chloride, p-toluenesulfonyl chloride, imidazolylsulfonyl chloride. More specifically, a method, which comprises allowing an unsaturated cyclitol derivative to react with sulfonyl halide (more than equimolar, preferably 1.2–3 mol.) in the presence of an organic base (e.g. tertiary amine such as triethylamine, pyridine, etc.) and, as the case may be, in an inert solvent such as dimethylformamide, benzene, toluene, acetone, etc., normally at −30° to 40° C. and, as the case may be especially at the initial stage of the reaction, under cooling to about −50° C., and, as the case may be, by heating up to about 80° C., is mentioned.

As the method, in Step B-7, of preparing the azido derivative (6) from the organic sulfonyl derivative (5) is exemplified the one which comprises allowing the compound (5) to react with, for example, an alkali metal azide such as sodium azide, lithium azide, etc., or a lower alkyl ammonium azide such as tetra-n-butyl ammonium azide, etc., in a organic solvent such as benzene, toluene, dimethylformamide, dimethyl acetamide, etc. or a mixed solvent of these solvents and water at an optional combination, normally in the range of −10° to 120° C. for 1–24 hours.

As the method, in Step B-8, of preparing the valienamine derivative (7) by subjecting the azido-derivative (6) to reduction, is exemplified a method of reducing by using an aluminium metal hydride such as lithium aluminium hydride, lithium trimethoxyaluminium hydride, lithium (tert-butoxy)aluminium hydride, etc. More specifically, the compound (7a) can be prepared by subjecting the compound (6) to reaction at −30° to 40° C. for 1–3 hours in a solvent such as tetrahydrofuran, ethyl ether, etc. using lithium aluminium hydride as the reducing agent.

Besides, as the method of selectively reducing the azido group to amino group, when a double bond is present in the azido-compound, are exemplified the method of reducing using alkali metal borohydride such as sodium borohydride, lithium borohydride, etc., and, as the case may be, in the presence of a phase-transfer catalyst such as hexadecyl tributylphosphonium bromide, etc.; the method of using propane-1,3-dithiol and triethylamine; the method of using chromous chloride ($CrCl_2$); the method of reducing the hydrogen sulfide in pyridine-water; the method of using triphenylphosphine; the method which comprises catalytic reduction using Lindler-catalyst; etc.

When the removal of the protective group of the hydroxyl group of the compound (7a) is necessary, the objective can be achieved by employing a known conventional deprotection method in accordance with the kind of the protective group then used.

For example, when tetrahydropyranyl group is the protective group for the hydroxyl group, valienamine (7b) can be prepared by conducting hydrolysis for 3–8 hours normally at 30°–80° C. in a mixture solution of acetic acid and water, for example.

Valiolamine can be prepared from the compound (7a) and the compound (7b) by, for example, the method shown in Scheme 5. Namely, valiolamine can be prepared through the following steps: the step of synthesizing the N-acyl derivative (8) by allowing the compound (7a) or the compound (7b) to react with a carbonylating agent representable by the general formula $R^7$—O—CO—Z (wherein Z stands for halogen atom, residue of active ester or residue of carbonic acid ester), the step of synthesizing the cyclic carbamate derivative (9) by allowing the compound (8) to react with a halogenating agent e.g. bromine, the step of synthesizing the compound (10) by reducing with a reductive dehalogenating agent e.g. sodium borohydride, the step of preparing compound (11a) or valiolamine (11b) by subjecting the cyclic carbamate linkage of the compound (10) to hydrolysis, and, if necessary, the step of removing the protective group for the hydroxyl group of the compound (11a). [Carbohyd. Res., 140, pp. 185–200 (1985)]

In each of the formulae of Scheme 5, $R^3$ stands for hydrogen atom or a protective group for hydroxyl group, $R^7$ stands for hydrocarbon residue of alkyl, aryl or aralkyl, and X stands for halogen atom. As the hydroxyl protective groups represented by $R^3$, those mentioned above as the hydroxyl protective group represented by $R^1$ can be similarly employed.

Scheme 5

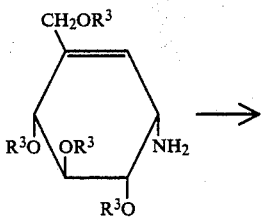

(7a): $R^3$ = hydroxyl protective group
(7b): $R^3$ = H

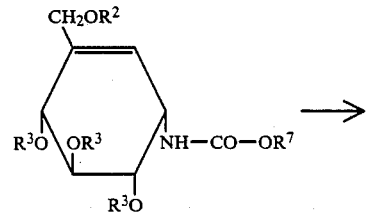

(8)

-continued
Scheme 5

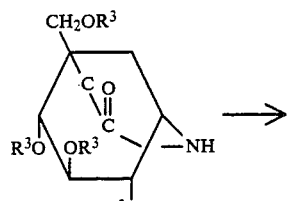

(9)

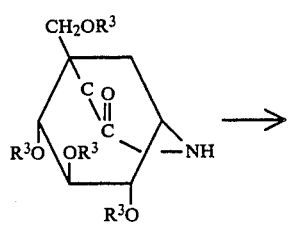

(10)

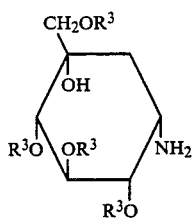

(11a): R³ = hydroxyl protective group
(11b): R³ = H

The obtained compounds [I'] and [III] and intermediates for synthesizing them can be isolated and purified by per se known means, for example, filtration, centrifugation, concentration, concentration under reduced pressure, drying, freeze-drying, adsorption, desorption, methods of utilizing difference of solubility to various solvents (e.g. solvent extraction, phasic transfer, precipitation, crystallization, recrystallization, etc.), chromatography (e.g. chromatography using ion-exchange resin, activated charcoal, high porous polymer, Sephadex, Sephadex ionexchanger, cellulose, ion-exchanging cellulose, silica gel, alumina, etc.), etc.

Salts of the compound [III] included in this invention are pharmaceutically acceptable addition salts of the compound [III]. As such salts, use is made of the salts of inorganic acids, e.g. hydrochloric acid, hydrobromic acid, sulfuric acid, phosphoric acid, nitric acid, etc., organic acids e.g. acetic acid, malic acid, citric acid, ascorbic acid, mandelic acid, methanesulfonic acid, etc., etc.

Further, the compound [III] wherein R³ is a hydrogen atom and the wavy bond〰〰〰is a S-configurational bond, representable by the general formula

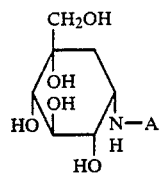

[wherein A is hydrogen atom or amine residue] i.e. valiolamine and N-substituted derivatives thereof and their salts are almost free from toxicity ($LD_{50}$ in rats, not lower than 500 mg/kg) and have α-glucosidase inhibitory activity, and suppress the metabolism of carbohydrates in man and other animals. Therefore, they suppress the rise of the blood sugar level and are useful for therapy and prophylaxis of hyperglycemic symptoms and various disorders caused by hyperglycemia such as diabetes, prediabetes, obesity, adipositas, hyperlipemia (arterioscelosis) as well as diseases attributable to sugar metabolism by microorganisms in oral cavity (for example, dental carries, etc.).

The compound [I] is a useful compound comparable to valiolamine as an intermediate for preparing various N-substituted valiolamine derivatives and other valiolamine-relating compounds.

Furthermore, it has been known that sedoheptulose usable as the starting material for preparing the compound [I'] is accumulated in a large amount in the culture broth of a certain species of bacteria or actinomycetes, etc., thus sedoheptulose can be prepared less expensively by fermentation production. Besides, sedoheptulosan or 2,7-anhydro-β-idoheptulopyranose (D-idoheptulosan) can be prepared less expensively by employing sedoheptulose as the starting material, and, therefore, the method of this invention is useful for preparing valiolamine and N-substituted valiolamine derivatives.

The unsaturated inosose derivative [I''] of the present invention is an important compound as starting material for preparing valienamine, valiolamine via valienamine, and their N-substituted derivatives. The inventors have succeeded in preparing the unsaturated inosose derivative [I''] via the compound [VIII] which is prepared from D-glucose or D-glucono-1,5-lactone obtainable from D-glucose inexpensively and easily.

The following Reference Examples and Examples illustrate in detail the content of the present invention, but the scope of the present invention should not be limited thereto. The mixture ratios of the mixed solvents used in Reference Examples and Examples are all shown by V/V, unless otherwise specified.

REFERENCE EXAMPLE 1

4,5-O-Isopropylidenesedoheptulosan

Crystals of sedoheptulosan(2,7-anhydro-β-D-altro-2-heptulopyranose, 25 g) were pulverized and suspended in acetone (320 ml). To the suspension was added conc. sulfuric acid (2.5 ml), and the mixture was stirred for 18 hours at room temperature. The resulting crystals were collected by filtration and washed with acetone to give 4,5-O-isopropylidenesedoheptulosan (28 g).

Elemental Analysis for $C_{10}H_{16}O_6$, Calcd (%): C, 51.72; H, 6.94, Found (%): C, 51.58; H, 6.97.

REFERENCE EXAMPLE 2

1,3-Di-O-benzoyl-4,5-O-isopropylidenesedoheptulosan

To a suspension of 4,5-O-isopropylidenesedoheptulosan (5.0 g) in a mixture solvent of N,N-dimethylformamide (DMF) (85 ml) and pyridine (5 ml) was added dropwise benzoyl chloride (9 ml) under cooling (about −30° C.). The mixture was stirred for further 2.5 hours at −5° to −10° C. The reaction solution was added to ice-water (about 200 ml) and the resulting oily product was subjected to extraction with ethyl acetate. The ethyl acetate extract solution was washed with 2N hydrochloric acid and saturated sodium hydrogencarbonate solution, which was then dried over anhydrous sodium sulfate. The solvent was distilled off under reduced pressure, and the residue was subjected to a silica gel column chromatography (500 ml), followed by elution with toluene-ethyl acetate (10:1). The eluate fractions were combined and concentrated to dryness under reduced pressure, and the residue was dried overnight under reduced pressure to give 1,3-di-O-benzoyl-4,5-O-isopropylidenesedoheptulosan as a white powder (8.8 g).

REFERENCE EXAMPLE 3

1,3-Di-O-benzoylsedoheptulosan

In 80% acetic acid (90 ml) was dissolved 1,3-di-O-benzoyl-4,5-O-isopropylidenesedoheptulosan (8.8 g), and the solution was stirred at 70° to 75° C. for 2 hours. To the reaction solution was added water (170 ml), which was concentrated under reduced pressure. The concentrate was dissolved in ethyl acetate, which was washed with saturated sodium hydrogencarbonate solution. The resultant was dried over anhydrous sodium sulfate, followed by distilling off the solvent. To the residue was added ethyl ether-petroleum ether (3:1) (280 ml). The mixture was left standing overnight in a refrigerator to give 1,3-di-O-benzoylsedoheptulosan as crystals (7.3 g).

REFERENCE EXAMPLE 4

1,3,4-Tri-O-benzoylsedoheptulosan

To a solution of 1,3-di-O-benzoylsedoheptulosan (14.1 g) in dichloromethane (140 ml) was added pyridine (4.7 ml), to which was added dropwise under cooling (−40° C. or below) a solution of benzoyl chloride (5.64 g) in dichloromethane (50 ml). The mixture was stirred for 2.5 hours under cooling (−40° to −30° C.). The reaction solution was poured into ice-water, which was stirred for 30 minutes. The dichloromethane layer was separated, and the aqueous layer was subjected to extraction with dichloromethane. The dichloromethane extract was washed with 2N hydrochloric acid and saturated sodium hydrogencarbonate solution, followed by drying over anhydrous sodium sulfate. From the resultant was distilled off the solvent under reduced pressure. To the residue was added ethyl ehtyl-petroleum ether (1:10) (1 l). The mixture was left standing overnight in a refrigerator to give crystals (17.5 g) of 1,3,4-tri-O-benzoylsedoheptulosan.

Elemental Analysis for $C_{28}H_{24}O_9$: Calcd. (%): C, 66.66; H, 4.80, Found (%): C, 67.04; H, 4.74.

NMR(CDCl$_3$)δ: 2.51(1H, d, J=6 Hz, —OH), 3.9–4.25(2H, m, 7—CH$_2$), 4.25-4.5[1H, m, 5—CH; changed to δ4.38(dd, J=3 Hz, 5 Hz) by the addition of D$_2$O], 4.58(2H, s, 1—CH$_2$), 4.7-4.9(1H, m, 6—CH), 5.46(1H, dd, J=3 Hz, 9 Hz, 4—CH), 5.94(1H, d, J=9 Hz, 3—CH), 7.1-7.7(9H, m) and 7.8–8.2(6H, m)(C$_6$H$_5$×3).

REFERENCE EXAMPLE 5

1,3,4-Tri-O-benzoyl-5-O-(imidazolylsulfonyl)sedoheptulosan

In DMF (100 ml) was dissolved 1,3,4-tri-O-benzoylsedoheptulosan (9.48 g). To the solution was added under cooling at −40° C. or below sulfuryl chloride (3.2 ml), and the mixture was stirred at about −40° C. for 20 minutes. The reaction solution was again cooled to −40° C. or below, to which was added imidazole (13.6 g). The cooling bath was removed, and then the mixture was stirred at room temperature for 1.5 hour. The reaction solution was poured into ice-water (300 ml), and the resulting oily substance was subjected to extraction with ethyl acetate. The ethyl acetate extract solution was washed with 2N hydrochloric acid and saturated sodium hydrogencarbonate solution, which was dried over anhydrous sodium sulfate, followed by distilling off the solvent under reduced pressure. The residue was subjected to a silica gel column chromatography (600 ml), followed by elution with toluene-ethyl acetate (3:2). The eluate was concentrated under reduced pressure, to which was added petroleum ether (about 100 ml). The mixture was left standing overnight in a refrigerator to give 1,3,4-tri-O-benzoyl-5-O-(imidazolylsulfonyl)sedoheptulosan as a white powder (9.5 g).

Elemental Analysis for $C_{31}H_{26}N_2O_{11}S$: Calcd. (%): C, 58.67; H, 4.13; N, 4.41, Found (%): C, 58.71; H, 4.10; N, 4.43.

NMR(CDCl$_3$)δ: 4.04(1H, dd, J=5 Hz, J=8 Hz, 7—CH), 4.08(1H, d, J=8 Hz, 7—CH), 4.59(2H, s, 1—CH$_2$), 4.75–4.90(1H, m, 6—CH), 5.27(1H, dd, J=2.5 Hz. 4 Hz, 5—CH), 5.49(1H, dd, J=4 Hz, 9.5 Hz, 4—CH), 5.92 (1H, d, J=9.5 Hz, 3—CH), 6.78, 7.15 and 7.18(each 1H, s, imidazole), 7.2–7.7(9H, m) and 7.8–8.2(6H, m)(C$_6$H$_5$×3).

REFERENCE EXAMPLE 6

2,7-Anhydro-1,3,4,5-tetra-O-benzoyl-β-D-ido-2-heptulopyranose

In toluene (140 ml) was dissolved 1,3,4-tri-O-benzoyl-5-O-(imidazolylsulfonyl)sedoheptulosan (9.5 g), to which was added tetra-n-butylammonium benzoate (11 g), and the mixture was stirred for 3 hours at 100° C. The solvent was then distilled off under reduced pressure. The residue was partitioned between ethyl acetate and water, and the aqueous layer was subjected to further extraction with ethyl acetate. The ethyl acetate layers were combined and washed with 2N hydrochloric acid and saturated sodium hydrogencarbonate solution, then dried over anhydrous sodium sulfate, followed by distilling off the solvent. The residue was subjected to a silica gel column chromatography (1 l) using a mixture of toluene-ethyl acetate (19:1) as the eluent. The eluate was subjected to concentration to dryness under reduced pressure to give a white powder (6.8 g) of 2,7-anhydro-1,3,4,5-tetra-O-benzoyl-β-ido-2-heptulopyranose.

Elemental Analysis for $C_{35}H_{28}O_{10}$: Calcd. (%): C, 69.07; H, 4.64, Found (%): C, 69.34; H, 4.67.

NMR(CDCl$_3$)δ: 4.02(1H, dd, J=4.5 Hz, 8 Hz, 7—CH), 4.50(1H, d, J=8 Hz, 7—CH), 4.60(2H, s, 1—CH$_2$), 5.10(1H, t, J=4.5 Hz, 6—CH), 5.54(1H, dd, J=4.5 Hz, 8.5 Hz, 5—CH), 5.80(1H, d, J=8.5 Hz,

3—CH), 6.80(1H, t, J=8.5 Hz, 4—CH), 7.2–7.7(12H, m) and 7.8–8.2(8H, m)(C$_6$H$_5$×4).

REFERENCE EXAMPLE 7

Methyl 1,3,4,5-tetra-O-benzoyl-D-ido-2-heptulopyranoside

In a mixture of methanol (30 ml) and methyl orthoformate (15 ml) was dissolved 2,7-anhydro-1,3,4,5-tetra-O-benzoyl-β-D-ido-2-heptulopyranose (3.0 g). To the solution was added zinc chloride (3.0 g), and the mixture was stirred at room temperature for 40 hours. The reaction solution was concentrated under reduced pressure, and the concentrate was partitioned between ethyl acetate and water. The ethyl acetate layer was washed with 2N hydrochloric acid and saturated sodium hydrogencarbonate solution, dried over anhydrous sodium sulfate, followed by distilling off the solvent. The residue was chromatographed on a column of silica gel (200 m) with toluene-ethyl acetate (5:1). The eluate was concentrated to dryness under reduced pressure to give a white powder (1.05 g) of methyl 1,3,4,5-tetra-O-benzoyl-D-ido-2-heptulopyranoside.

Elemental Analysis for C$_{36}$H$_{32}$O$_{11}$: Calcd (%): C, 67.49; H, 5.03, Found (%): C, 66.98; H, 4.74.

NMR(CDCl$_3$)δ: 2.36(1H, broad s, —OH), 3.69(3H, s, —OCH$_3$), 3.97(1H, dd, J=6.5 Hz, 9.5 Hz, 7—CH), 4.21(1H, dd, J=7 Hz, 9.5 Hz, 7—CH), 4.56(2H, s, 1—CH$_2$), 4.60–4.75(1H, m, 6—CH), 5.31(1H, dd, J=5 Hz, 8.5 Hz, 5—CH), 5.82(1H, d, J=8.5 Hz, 3—CH), 5.96 (1H, t, J=8.5 Hz, 4—CH), 7.15–7.7(12H, m) and 7.8–8.2(8H, m)(C$_6$H$_5$×4).

REFERENCE EXAMPLE 8

Methyl 1,3,4,5-tetra-O-benzoyl-7-deoxy-7-iodo-D-iodo-2-heptulopyranoside

In DMF (16 ml) was dissolved methyl 1,3,4,5-tetra-O-benzoyl-D-ido-2-heptulopyranoside (950 mg). To the solution were added triphenyl phosphine (1.65 g) and N-iodosuccinimide (1.2 g). The mixture was stirred at room temperature overnight. To the mixture was added ice-water (100 ml). The resulting oily substance was subjected to extraction with ethyl acetate. The ethyl acetate extract was washed with saturated sodium thiosulfate solution, 2N hydrochloric acid and saturated sodium hydrogencarbonate solution, dried over anhydrous sodium sulfate, followed by distilling off the solvent under reduced pressure. The residue was chromatographed on a column of silica gel (200 ml) with toluene-ethyl acetate (10:1). The eluate was concentrated to dryness under reduced pressure to give a white powder (780 mg) of methyl 1,3,4,5-tetra-O-benzoyl-7-deoxy-7-iodo-D-ido-2-heptulopyranoside.

REFERENCE EXAMPLE 9

Methyl 1,3,4,5-tetra-O-benzoyl-7-deoxy-L-xylo-2-hept-6-enoulopyranoside [namely, methyl 1,3,4,5-tetra-O-benzoyl-7-deoxy-D-ido-2-hept-6-enoulopyranoside]

In pyridine (5 ml) was dissolved methyl 1,3,4,5-tetra-O-benzoyl-7-deoxy-7-iodo-D-ido-2-heptulopyranoside (500 mg). To the solution was added silver fluoride (1.0 g), which was stirred at room temperature for 18 hours. To the reaction solution was added ethyl ether (100 ml), and insolubles were filtered off and washed with ethyl ether. The filtrate and the washings were combined and concentrated under reduced pressure. The concentrate was dissolved in ethyl acetate and washed with 2N hydrochloric acid and saturated aqueous sodium hydrogencarbonate, dried over anhydrous sodium sulfate, followed by distilling off the solvent under reduced pressure. The residue was chromatographed on a column of silica gel (100 ml) using toluene-ethyl acetate (9:1) as the eluent. The elute was concentrated to dryness under reduced pressure to give a white powder (249 mg) of methyl 1,3,4,5-tetra-O-benzoyl-7-deoxy-L-xylo-2-hept-6-enoulopyranoside.

Elemental Analysis for C$_{36}$H$_{30}$O$_{10}$: Calcd. (%): C, 69.56; H, 4.86, Found (%): C, 70.03; H, 5.09.

NMR(CDCl$_3$)δ: 3.68(3H, s, —OCH$_3$), 4.45(2H, broad s, 1—CH$_2$), 5.32(1H, d, J=9 Hz, 5—CH or 3—CH), 5.64(1H, d, J=9 Hz, 3—CH or 5—CH), 5.81 (1H, t, J=9 Hz, 4—CH), 5.91 and 6.03 (each 1H, s, 7—CH$_2$), 7.2–7.7(12H, m) and 7.8–8.2(8H, m) (C$_6$H$_5$×4).

REFERENCE EXAMPLE 10

(1S)-(1(OH),2,4,5/1,3)-1-C-(Hydroxymethyl)-1,2,3,4,5-cyclohexanepentol and (1S)-(1(OH),2,4/1,3,5)-1-C-(hydroxymethyl)-1,2,3,4,5-cyclohexanepentol Sodium borohydride (250 mg) was added to a solution of 2D-(2,4,5(OH)/3,5)-2,3,4-tri-O-benzoyl-5-(benzoyloxymethyl)-2,3,4,5-tetrahydroxycyclohexanone (1.0 g) in methanoltetrahydrofuran (1:1, 30 ml) with cooling (ice-water bath) and stirred for 2 hours at the same temperature. The mixture was concentrated and then partitioned between ethyl acetate and water. The ethyl acetate layer was washed with 2N hydrochloric acid and saturated aqueous sodium hydrogencarbonate, dried with anhydrous sodium sulfate, and then evaporated in vacuo. The residue was dissolved in methanol-acetone-2N sodium hydroxide (2:6:3, 220 ml) and stirred overnight at room temperature. The mixture was evaporated in vacuo. Water (50 ml) was added to the residue and then the mixture was filtered. The filtrate was passed through a column of Dowex 50W×8 (H$^+$ type, 250 ml). The column was washed with water and the eluate was concentrated in vacuo. The residue was choromatographed on a column of Dowex 1×2 (OH$^-$ type, 400 ml) and the column was eluted with water. The eluate was separated to the earlier eluted fraction (570 to 760 ml) and the later eluted fraction (765 to 1050 ml). The later eluted fraction was concentrated in vacuo and re-chromatographed on a column of Dowex 1×2 (OH$^-$ type, 600 ml). The eluate was again separated to the earlier eluted fraction (0.75 to 1.03 ml) and the later eluted fraction (1.1 to 1.4 l). The later eluted fraction was concentrated in vacuo then lypophilized to give (1S)-(1(OH),2,4,5/1,3)-1-C-(hydroxymethyl)-1,2,3,4,5-cyclohexanepentol (49 mg) as a white powder. The earlier eluted fractions of the first and the second Dowex 1×2 coumn chromatographic runs were combined, concentrated in vacuo and then lyophilized to give (1S)-(1(OH),2,4/1,3,5)-1-C-(hydroxymethyl)-1,2,3,4,5-cyclohexanepentol (68 mg) as a white powder.

(1S)-(1(OH),2,4/1,3,5)-1-C-(hydroxymethyl)-1,2,3,4,5-cyclohexanepentol (the earlier eluted isomer):

NMR (D$_2$O) δ: 1.63 (1H, dd, J=12 Hz, 14 Hz), 2.14 (1H, dd, J=5 Hz, 14 Hz), 3.25–4.1 (6H, m).

(1S)-(1(OH),2,4,5/1,3)-1-C-(hydroxymethyl)-1,2,3,4,5-cyclohexanepentol (the later eluted isomer):

NMR (D$_2$O) δ: 1.79 (1H, dd, J=3 Hz, 15.5 Hz), 2.12 (1H, dd, J=4 Hz, 15.6 Hz), 3.4–4.45 (6H, m).

REFERENCE EXAMPLE 11

2,3,4,6-Tetra-O-(tetrahydropyranyl)-D-glucono-1,5-lactone

To a solution of D-glucono-1,5-lactone (20 g) in N,N-dimethylformamide (50 ml) was added p-toluenesulfonic acid (0.5 g). To the mixture was added dropwise with cooling with ice-water 3,4-dihydro-2H-pyran (100 ml), followed by stirring for two hours at the same temperature, then for one hour at room temperature. The reaction solution was added to a mixture of ethyl acetate (1.2 l) and water (0.4 l). The ethyl acetate layer was separated, washed with saturated sodium hydrogencarbonate solution, dried over anhydrous sodium sulfate, followed by concentration under reduced pressure. The residue was subjected to a silica gel column chromatography (1.5 l). The column was washed with toluene, and then elution was conducted with toluene-ethyl acetate (9:1). The eluate was concentrated and then dried under reduced pressure to give 2,3,4,6-tetra-O-(tetrahydropyranyl)-D-glucono-1,5-lactone (54.7 g).

IR: $\nu_{max}^{neat}$ 1765 cm$^{-1}$

Elemental Analysis for $C_{26}H_{42}O_{10}$: Calcd. (%): C, 60.68; H, 8.23, Found (%): C, 61.21; H, 8.17.

REFERENCE EXAMPLE 12

3,4,5,7-Tetra-O-benzyl-1-deoxy-1-(dimethoxyphosphoryl)-D-gluco-2-heptulopyranose In tetrahydrofuran (50 ml) was dissolved dimethyl methylphosphonate (4.4 ml), to which was added dropwise a solution of n-butyllithium in n-hexane (1.7M solution, 17 ml) with cooling ($-70°$ to $-78°$ C.) in a stream of argon, and the mixture was stirred for 30 minutes. To the solution was added dropwise with cooling at the same temperature a solution of 2,3,4,6-tetra-O-benzyl-D-glucono-1,5-lactone (5.3 g) in tetrahydrofuran (25 ml). The mixture was stirred for 30 minutes. The cooling bath was removed, and the mixture was allowed to warm to 0° C. with stirring.

The reaction solution was added to an ice-cooled mixture of 10% (W/V) ammonium chloride solution (100 ml) and ethyl acetate (300 ml). The ethyl acetate layer was separated, washed with water, dried over anhydrous sodium sulfate, and then concentrated under reduced pressure. The residue was subjected to a silica gel column chromatography (400 ml), followed by elution with toluene-ethyl acetate (2:1). The eluate was concentrated under reduced pressure, and dried under reduced pressure to give 3,4,5,7-tetra-O-benzyl-1-deoxy-1-(dimethoxyphosphoryl)-D-gluco-2-heptulopyronose (6.0 g). $[\alpha]_D^{26}$ $-12.5°$ (c=1, CHCl$_3$).

$^1$HNMR(CDCl$_3$)$\delta$: 1.69(dd, J=15, 19 Hz) and 2.32 (dd, J=15, 18 Hz) (each 1H, —CH$_2$P—), 3.60(3H, d, J=11 Hz, —OCH$_3$), 3.66(3H, d, J=11 Hz, —OCH$_3$).

Elemental Analysis for $C_{37}H_{43}O_9P$: Calcd. (%): C, 67.06; H, 6.54, Found (%): C, 67.15; H, 6.54.

REFERENCE EXAMPLE 13

3,4,5,7-Tetra-O-(tetrahydropyranyl)-1-deoxy-1-(dimethoxyphosphoryl)-D-gluco-2-heptulopyranose To a solution of dimethyl methylphosphonate (15.3 ml) in ethyl ether (300 ml) was added dropwise with cooling ($-70°$ to $-78°$ C.) in a stream of argon a solution of n-butyllithium in n-hexane (1.6M solution, 84 ml), and the mixture was stirred for 30 minutes. To the solution was added dropwise with cooling at the same temperature a solution of 2,3,4,6-tetra-O-(tetrahydropyranyl)-D-glucono-1,5-lactone (23.1 g) in ethyl ether (80 ml). The mixture was stirred for one hour, then the cooling bath was removed, and then the mixture was allowed to warm to 0° C. with stirring. The reaction solution was added to an ice-cooled mixture of 10%(W/V) ammonium chloride solution (250 ml) and ethyl ether (120 ml). The ethyl ether layer was separated. The aqueous layer was subjected to extraction with ethyl ether. The organic layers were combined, washed with water, dried over anhydrous magnesium sulfate, concentrated under reduced pressure, and dried further under reduced pressure to give 3,4,5,7-tetra-O-(tetrahydropyranyl)-1-deoxy-1-(dimethoxyphosphoryl)-D-gluco-2-heptulopyranose (26.6 g).

$[\alpha]_D^{26}$ $+34.6°$ (C=1, CHCl$_3$), $^1$HNMR(CDCl$_3$)$\delta$: 3.72(6H, d, J=12 Hz, —OCH$_3\times2$).

Elemental Analysis for $C_{29}H_{51}O_{13}P$: Calcd. (%): C, 54.54; H, 8.05, Found (%): C, 54.83; H, 8.18.

REFERENCE EXAMPLE 14

3,4,5,7-Tetra-O-benzyl-1-deoxy-1-(dimethoxyphosphoryl)-D-glycero-D-gulo-heptitol and
1,3,4,5-tetra-O-benzyl-7-deoxy-7-(dimethoxyphosphoryl)-D-glycero-L-gulo-heptitol To a solution of 3,4,5,7-tetra-O-benzyl-1-deoxy-1-(dimethoxyphosphoryl)-D-gluco-2-heptulopyranose (13.8 g) in tetrahydrofuran (140 ml) was added sodium borohydride (1.4 g). The mixture was stirred overnight at room temperature. The reaction mixture was concentrated under reduced pressure, and the residue was distributed between ethyl acetate (500 ml) and water (300 ml). The ethyl acetate layer was washed with water, dried over anhydrous sodium sulfate and concentrated under reduced pressure. The concentrate was subjected to a silica gel column chromatography (550 ml) with tolueneacetone (2:1). The elute was concentrated under reduced pressure and dried under reduced pressure to give a mixture (12.4 g) of 3,4,5,7-tetra-O-benzyl-1-deoxy-1-(dimethoxyphosphoryl)-D-glycero-D-gulo-heptitol and 1,3,4,5-tetra-O-benzyl-7-deoxy-7-(dimethoxyphosphoryl)-D-glycero-L-gulo-heptitol.

$[\alpha]_D^{26}$ $+1.7°$ (c=1, CHCl$_3$), $^1$HNMR(CDCl$_3$)$\delta$: 1.5–2.3 (2H, m, —CH$_2$P—), 3.04 (2H, broad s, —OH$\times2$), 3.63 and 3.66 (total 6H, d, J=11 Hz, —OCH$_3\times2$)

Elemental Analysis for $C_{37}H_{45}O_9P$: Calcd. (%): C, 66.86; H, 6.82; P, 4.66, Found (%): C, 66.91; H, 6.93; P, 4.81.

REFERENCE EXAMPLE 15

3,4,5,7-Tetra-O-(tetrahydropyranyl)-1-deoxy-1-(dimethoxyphosphoryl)-D-glycero-D-gulo-heptitol and
1,3,4,5-tetra-O-(tetrahydropyranyl)-7-deoxy-7-(dimethoxyphosphoryl)-D-glycero-L-gulo-heptitol To a solution of 3,4,5,7-tetra-O-(tetrahydropyranyl)-1-deoxy-1-(dimethoxyphosphoryl)-D-gluco-2-heptulopyranose (26.6 g) in diethyl ether (300 ml) was added sodium borohydride (3.0 g). The mixture was stirred overnight at room temperature. Insolubles were filtered off and washed with diethyl ether. The filtrate and the washings were combined, washed with 10%(W/V) sodium chloride solution, and dried over anhydrous magnesium sulfate, followed by concentration under reduced pressure. The concentrate was chromatographed on a column of silica gel (1 l) with tolueneacetone (1:1). The eluate was concentrated under reduced pressure and dried under reduced pressure to give a mixture (18.8 g) of 3,4,5,7-tetra-O-(tetrahydropyranyl)-1-deoxy-1-(dimethoxyphosphoryl)-D-glycero-D-gulo-heptitol and 1,3,4,5-tetra-O-(tetrahydropyranyl)-7-deoxy-7-(dimethoxyphosphoryl-D-glycero-L-gulo-heptitol.

$[\alpha]_D^{26}$ +12.6° (c=1, CHCl$_3$).

Elemental Analysis for C$_{29}$H$_{53}$O$_{13}$P: Calcd. (%): C, 54.36; H, 8.34, Found (%): C, 54.73; H, 8.57.

REFERENCE EXAMPLE 16

3,4,5,7-Tetra-O-benzyl-1-deoxy-1-(dimethoxyphosphoryl)-D-xylo-2,6-heptodiulose

A solution of dimethylsulfoxide (8.1 ml) in dichloromethane (87 ml) was cooled at −65° C. to −75° C., to which was added dropwise a solution of trifluoroacetic anhydride (9.83 ml) in dichloromethane (40 ml). The mixture was stirred for 30 minutes, to which was added dropwise a solution of a mixture (11.6 g) of 3,4,5,7-tetra-O-benzyl-1-deoxy-1-(dimethyoxyphosphoryl)-D-glycero-D-gulo-heptitol and 1,3,4,5,-tetra-O-benzyl-7-deoxy-7-(dimethoxyphosphoryl)-D-glycero-L-gulo-heptitol in dichloromethane (80 ml). The mixture was stirred for one hour at the same temperature. To the reaction mixture while cooling at the same temperature was added dropwise triethylamine (23.2 ml), and the mixture was stirred for 30 minutes. The cooling bath was removed, and the mixture was allowed to warm to 0° C. with stirring. The reaction solution was added to an ice-cooled mixture of dichloromethane (300 ml) and 2N hydrochloric acid (250 ml). The dichloromethane layer was separated, washed with a saturated sodium hydrogencarbonate solution, dried over anhydrous magnesium sulfate and concentrated under reduced pressure. The residue was chromatographed on a column of silica gel (500 ml) with tolueneethyl acetate (1:1). The eluate was concentrated under reduced pressure and dried under reduced pressure to give 3,4,5,7-tetra-O-benzyl-1-deoxy-1-(dimethoxyphosphoryl)-D-xylo-2,6-heptodiulose (11.5 g).

$[\alpha]_D^{23}$ −28.5° (c=1, CHCl$_3$), IR: $\nu_{max}^{CHCl_3}$1733, 1704 cm$^{-1}$ (C=O).

Elemental Analysis for C$_{37}$H$_{41}$O$_9$P: Calcd. (%): C, 67.26; H, 6.25; P, 4.69, Found (%): C, 67.70; H, 6.32; P, 4.69.

REFERENCE EXAMPLE 17

3,4,5,7-Tetra-O-(tetrahydropyranyl)-1-deoxy-1-(dimethoxyphosphoryl)-D-xylo-2,6-heptodiulose To a solution of dimethylsulfoxide (9.4 ml) in dichloromethane (100 ml) was added dropwise, while cooling at −65° C. to −75° C., a solution of trifluoroacetic anhydride (12.3 ml) in dichloromethane (50 ml). The mixture was stirred for 30 minutes, to which was then added dropwise a solution of a mixture (14.0 g) of 3,4,5,7-tetra-O-(tetrahydropyranyl)-1-deoxy-1-(dimethoxyphosphoryl)-D-glycero-D-gulo-heptitol and 1,3,4,5-tetra-O-(tetrahydropyranyl)-7-deoxy-7-(dimethoxyphosphoryl)-D-glycero-L-gulo-heptitol in dichloromethane (70 ml). The reaction mixture was stirred for one hour at the same temperature. To the solution was added dropwise, while cooling at the same temperature, a solution of triethylamine (27.5 ml) in dichloromethane (50 ml), and the mixture was stirred for 30 minutes. The cooling bath was removed, and the mixture was allowed to warm to 0° C. with stirring. The reaction solution was added an ice-cooled mixture of dichloromethane (200 ml) and 2N hydrochloric acid (200 ml). The dichloromethane layer was separated, washed with saturated sodium hydrogencarbonate solution, dried over anhydrous sodium sulfate, and then concentrated under reduced pressure. The residue was chromatographed on a column of silica gel (500 ml) with toluene-acetone (2:1). The eluate was concentrated under reduced pressure and dried in vacuo to give 3,4,5,7-tetra-O-(tetrahydropyranyl)-1-deoxy-1-(dimethoxyphosphoryl)-D-xylo-2,6-heptodiulose (12.4 g).

$[\alpha]_D^{26}$ +39.3° (c=1, CHCl$_3$), IR: $\nu_{max}^{neat}$ 1738 cm$^{-1}$ (C=O)

REFERENCE EXAMPLE 18

3,4,5,7-Tetra-O-benzyl-1-deoxy-1-(dimethoxyphosphoryl)-D-gluco-2-heptulopyranose A solution of n-butyllithium in n-hexane (1.6M solution, 68.8 ml) was added to a solution of dimethyl methylphosphonate (13.65 g) in tetrahydrofuran (200 ml) in a stream of argon at −70° to −78° C., and then stirred for 30 min. To the solution was added a solution of 2,3,4,6-tetra-O-benzyl-D-glucono-1,5-lactone (29.6 g) in tetrahydrofuran (150 ml) at −70° to −78° C. The mixture was stirred for 1 hour at the same temperature. The cooling bath was removed and the mixture was allowed to warm to 0° C. with stirring. Ice-cold 10% ammonium chloride solution (400 ml) was added to the reaction mixture and the resulting oily substances were extracted with ethyl acetate (1.2 l). The ethyl acetate solution was washed with 2N hydrochloric acid and saturated aqueous sodium hydrogen-carbonate, dried with anhydrous sodium sulfate and then evaporated in vacuo. Ethyl ether-petroleum ether (1:3; 400 ml) was added to the residue and the mixture was refrigerated to give 3,4,5,7-tetra-O-benzyl-1-deoxy-1-(dimethoxyphosphoryl)-D-gluco-2-heptulopyranose (33.1 g) as white crystals; m.p. 112°–113° C.;

$[\alpha]_D^{23}$ −15.6° (c=1, CHCl$_3$); $^1$H−n.m.r. (CDCl$_3$): δ1.69 (dd, J=15 Hz, 19 Hz) adn 2.32 (dd, J=-Hz, 18 Hz) (each 1H, —CH$_2$—), 3.60(d, 3H, J=11 Hz, —OCHHd 3), 3.66 (d, 3H, J=11 Hz, OCH$_3$).

Elemental Analysis for C$_{37}$H$_{43}$O$_9$P: Calcd. (%): C, 67.06; H, 6.54; P,4.67, Found (%): C, 67.09; H, 6.39; P, 4.82.

REFERENCE EXAMPLE 19

4L-4,6/5-Tri(benzyloxy)-3-(benzyloxymethyl)-2-cyclohexenone oxime

Hydroxylamine hydrochloride (2.0 g) was added to a solution of 4L-4,6/5-tri(benzyloxy)-3-(benzyloxymethyl)-2-cyclohexenone (2.0 g) in dimethyl sulfoxide (10 ml) and then stirred for 24 hours at room temperature. The mixture was distributed between ethyl acetate (250 ml) and water (150 ml). The organic layer was separated, washed with 2N hydrochloric acid and aqueous sodium hydrogencarbonate, dried with anhydrous sodium sulfate and then evaporated in vacuo. The residue was chromatographed on a column of silica gel (250 ml) with toluene-ethyl acetate (10:1). The eluate (450 to 800 ml) was evaporated and dried in vacuo to give the oxime (1.27 g) as a colorless syrup.

Elemental Analysis for C$_{35}$H$_{35}$NO$_5$: Calcd. (%): C, 76.48; H, 6.42; N, 2.55, Found (%): C, 76.66; H, 6.32; N, 2.35.

EXAMPLE 1

2D-2,3,4-tri-O-benzoyl-(2,4,5(OH)/3,5)-5-(benzoyloxymethyl)-2,3,4,5-tetrahydroxycyclohexanone In 80% acetone-water (40 ml) was dissolved methyl 1,3,4,5-tetra-O-benzoyl-7-deoxy-L-xylo-2-hept-6-enoulopyranoside [namely, methyl 1,3,4,5-tetra-O-benzoyl-7-deoxy-D-ido-2-hept-6-enoulopyranoside] (620 mg). To the solution was added mercuric chloride (275 mg), and the mixture was stirred at room temperature for 8 hours. The reaction solution was concentrated under reduced pressure to a volume of about 20 ml. To the concentrate were added ethyl acetate (100 ml) and water (100 ml). The mixture was stirred, and the ethyl acetate layer was separated, washed with 2N hydrochloric acid and saturated sodium hydrogencarbonate solution, dried over anhydrous sodium sulfate, followed by distilling off the solvent under reduced pressure. The residue was chromatographed on a column of silca gel (60 ml) with toluene-ethyl acetate (5:1). The eluate was concentrated to dryness under reduced pressure to give a white powder (248 mg) of 2D-2,3,4-tri-O-benzoyl-(2,4,5(OH)/3,5)-5-(benzoyloxymethyl)-2,3,4,5-tetrahydroxycyclohexanone.

Elemental Analysis for $C_{35}H_{28}O_{10}$: Calcd. (%): C, 69.07; H, 4.64, Found (%): C, 68.74; H, 5.03.

NMR(CDCl$_3$)δ: 2.38(1H, broad s, —OH), 2.88 and 3.04(each 1h, ABq, J=14.5 Hz, 6—CH$_2$), 4.81(2H, s, —CH$_2$O—), 5.43(1H, d, J=10 Hz, 4—CH), 5.81(1H, t, J=10 Hz, 3—CH), 6.11(1H, d, J=10 Hz, 2—CH), 7.2-7.7(2H, m) and 7.8-8.3(8H, m) ($C_6H_5 \times 4$). $[\alpha]_D^{22}$ −28.2° (c=1, CHCl$_3$).

Thin-layer chromatography (TLC; silica gel 60F-254, manufactured by Merck): toluene-ethyl acetate (2:1), Rf 0.52; toluene-acetone (9:1), Rf 0.31; n-hexane ethyl acetate (3:2), Rf 0.38.

Solubility: soluble in methanol, ethyl acetate, toluene, acetone, chloroform, insoluble in water, petroleum ether.

EXAMPLE 2

(1S)-(1(OH),2,4,5/1,3)-5-[[2-hydroxy-1-(hydroxymethyl)ethyl]amino]-1-C-(hydroxymethyl)-1,2,3,4-cyclohexanetetrol In acetic acid-ethanol (1:9, 15 ml) were dissolved 2D-2,3,4-tri-O-benzoyl-(2,4,5(OH)/3,5)-5-(benzoyloxymethyl)-2,3,4,5-tetrahydroxycyclohexanone (410 mg) and 2-amino-1,3-propanediol (280 mg). The solution was stirred at room temperature for 30 minutes, to which was added sodium cyanoborohydride (300 mg). The mixture was stirred at room temperature overnight. The reaction solution was concentrated to dryness under reduced pressure, and the concentrate was dissolved in methanol-acetone-1N sodium hydroxide (1:1:2, 100 ml). The solution was stirred at room temperature for 5.5 hours, followed by distilling off the organic solvent under reduced pressure. The concentrated solution was adjusted to pH 1 with 2N hydrochloric acid, which was washed with ethyl acetate. To the resultant was added Dowex 50W×8 (H+, 100 ml), and the mixtue was stirred at room temperature for 30 minutes. The reaction mixture was poured onto a column packed with Dowex 50W×8 (H+, 50 ml), then the column was washed with water, followed by performing elution with 0.5N ammonia water. The eluate was concentrated under reduced pressure. The concentrate was chromatographed on a column of Amberlite CG-50(NH$_4$+, 250 ml) with water. The eluate was concentrated under reduced pressure, to which was added ethanol. The mixture was refluxed for 15 minutes, followed by concentration under reduced pressure. The concentrate (about 2 ml) was left standing overnight to give a white powder of (1S)-(1(OH),2,4,5/1,3)-5-[[2-hydroxy-1-(hydroxymethyl)ethyl]amino]-1-C-(hydroxymethyl)-1,2,3,4-cyclohexanetetrol.

$[\alpha]_D^{24}$ +26.9° (c=1, H$_2$O), NMR(D$_2$O)δ: 1.54(1H, dd, J=3 Hz, 15 Hz, 6—CHax), 2.10(1H, dd, J=3 Hz, 15 Hz, 6—CHeq), 2.90(1H, quint., J=5 Hz, —N—CH), 3.35–4.0(10H, m).

EXAMPLE 3

(1S)-(1(OH),2,4,5/1,3)-5-[(2-hydroxyethyl)amino]-1-C-(hydroxymethyl)-1,2,3,4-cyclohexanetetrol and
(1S)-(1(OH),2,4/1,3,5)-5-[(2-hydroxyethyl)amino]-1-C-(hydroxymethyl)-1,2,3,4-cyclohexanetetrol In methanol (50 ml) were dissolved 2D-2,3,4-tri-O-benzoyl-(2,4,5(OH)/3,5)-5-(benzoyloxymethyl)-2,3,4,5-tetrahydroxycyclohexanone (880 mg) and ethanolamine (1.0 ml). To the solution was added sodium cyanoborohydride (1.0 g), and the mixture was stirred at room temperature overnight. The reaction solution was concentrated under reduced pressure, and the concentrate was partitioned between water (50 ml) and ethyl acetate (50 ml). The ethyl acetate layer was separated, and the aqueous layer was further subjected to extraction with ethyl acetate. Ethyl acetate layers were combined and washed with saturated sodium chloride solution, dried over anhydrous sodium sulfate, followed by concentration under reduced pressure. The concentrate was dissolved in methanol (130 ml), to which was added 1N sodium hydroxide (70 ml). The mixture was stirred at room temperature over night. The reaction solution was adjusted to pH 4 with 2N hydrochloric acid, followed by concentration under reduced pressure. The concentrate was partitioned between water (50 ml) and ethyl acetate (50 ml). The aqueous layer was separated and washed further with ethyl acetate, which was allowed to be adsorbed on a column of Dowex 50W×8 (H+, 400 ml). The column was then washed with water, then elution was conducted with 0.5N ammonia water. The eluate was concentrated under reduced pressure. The eluate was allowed to be adsorbed on a column of Amberlite CG-50(NH$_4$+, 250 ml). The column was washed with water, then elution was performed with 0.1N ammonia water. The eluate was concentrated to dryness under reduced pressure, and the concentrate was chromatographed on a column of Dowex 1×2 (OH−, 400 ml), then elution was performed with water. The earlier eluted fractions of the eluate (360–480 ml) were concentrated under reduced pressure, followed by freeze-drying to give (1S)-(1(OH),2,4/1,3,5)-5-[(2-hydroxyethyl)-amino]-1-C-(hydroxymethyl)-1,2,3,4-cyclohexanetetrol (59 mg), and the later eluted fractions (520–680 ml) were concentrated under reduced pressure, followed by freeze-drying to give (1S)-(1(OH),2,4,5/1,3)-5-[(2-hdyroxyethyl)amino]-1-C-(hydroxymethyl)-1,2,3,4-cyclohexanetetrol (228 mg).

(1S)-(1(OH),2,4/1,3,5)-5-[(2-hydroxyethyl)amino]-1-C-(hydroxymethyl)-1,2,3,4-cyclohexanetetrol (the earlier eluted isomer):

NMR (D$_2$O)δ: 1.16(1H, t, J=12 Hz, 6-CHax), 2.50(1H, dd, J=4 Hz, 12 Hz, 6-CHeq), 2.50–3.05(3H, m, 5-CH, N-CH$_2$), 3.25–3.95(7H, m).

(1S)-(1(OH),2,4,5/1,3)-5-[(2-hydroxyethyl)amino]-1-C-(hydroxymethyl)-1,2,3,4-cyclohexanetetrol (the later eluted isomer):

NMR (D$_2$O)δ: 1.52(1H, dd, J=3 Hz, 15 Hz, 6-CHax), 2.14(1H, dd, J=3.5 Hz, 15 Hz, 6-CHeq), 2.25–3.15(2H, m, N-CH$_2$), 3.25(1H, q, J=3 Hz, 5-CH), 3.34–4.0(7H, m).

Elemental analysis for C$_9$H$_{19}$NO$_6$: Calcd. (%): C, 45.56; H, 8.07; N, 5.90, Found (%): C, 45.59; H, 8.03; N, 5.99.

EXAMPLE 4

(1S)-(1(OH),2,4,5/1,3)-5-[[(R)-α-(hydroxymethyl)benzyl]-amino]-1-C-(hydroxymethyl)-1,2,3,4-cyclohexanetetrol In DMF (45 ml) were dissolved 2D-(2,4,5(OH)/3,5)-2,3,4-tri-O-benzoyl-5-(benzoyloxymethyl)-2,3,4,5-tetrahydroxycyclohexanone (860 mg) and D-phenylglycinol.acetate (950 mg). To the solution was added sodium cyanoborohydride (650 mg), and the mixture was stirred at 55° C. for 12 hours. The reaction solution was concentrated under reduced pressure, and the concentration was partitioned in ethyl acetate (100 ml) and water (50 ml). The ethyl acetate layer was washed with 2% acetic acid and saturated sodium hydrogencarbonate solution, dried over anhydrous sodium sulfate, then concentrated under reduced pressure. The concentrate was dissolved in methanol-acetone (5:3, 80 ml), to which was added 1N NaOH (20 ml), followed by stirring at room temperature for 3.5 hours. The reaction solution was adjusted to pH 3 with 2N HCl, which was then concentrated under reduced pressure. The concentrate was partitioned between water (100 ml) and ethyl acetate (50 ml). The aqueous layer was separated and washed with ethyl acetate, which was then chromatographed on a column of Dowex 50W×8 (H$^+$, 150 ml). The column was washed with water, then elution was conducted by using 0.5N ammonia water. The eluate was concentrated under reduced pressure, and the concentrate was chromatographed on a column of Amberlite CG-50 (NH$_4^+$, 180 m) with water. The eluate was concentrated under reduced pressure, which was then left standing in a refrigerator to give N-[(R)-α-(hydroxymethyl)benzyl]valiolamine as white crystals (150 mg). m.p. 157°–158° C.,

[α]$_D^{24}$ −10.6° (c=1, H$_2$O), −6.5° (c=1 0.1N HCl); NMR (D$_2$O)δ: 1.43(1H, dd, J=3.5 Hz, 15 Hz, 6-CHax), 1.73(1H, dd, J=3.5 Hz, 15 Hz, 6-CHeq), 3.25–3.7(4H, m), 3.7–4.0(5H, m), 7.58(5H, s, Ph).

EXAMPLE 5

(1S)-(1(OH),2,4,5/1,3)-5-amino-1-C-(hydroxymethyl)-1,2,3,4-cyclohexanetetrol (valiolamine)

(a) To a methanolic solution (200 ml) of 2D-(2,4,5(OH)/3,5)-2,3,4-tri-O-benzoyl-5-(benzoyloxymethyl)-2,3,4,5-tetrahydroxycyclohexanone (1.0 g) were added hydroxylamine hydrochloride (400 mg) and pyridine (2 ml), and the mixture was stirred overnight at room temperature. The reaction solution was concentrated under reduced pressure. The concentrate was partitioned between ethyl acetate (100 ml) and water (20 ml), and the ethyl acetate layer was separated, washed with 2N HCl, saturated sodium hydrogencarbonate solution and water, dried over anhydrous sodium sulfate and concentrated to dryness in vacuo. The residue was subjected to a silica gel (ca. 100 ml) column chromatography. The column was washed with toluene-ethyl acetate (10:1), followed by elution with toluene-ethyl acetate (5:1). The eluate was concentrated to dryness under reduced pressure to give 2D-(2,4,5(OH)/3,5)-2,3,4-tri-O-benzoyl-5-(benzoyloxymethyl)-2,3,4,5-tetrahydroxycyclohexanone oxime as white powder (410 mg).

(b) In methanol (20 ml) was dissolved the above-mentioned cyclohexanone oxime (410 mg), to which was added conc. ammonium water (4 ml). The mixture was stirred at room temperature overnight. To the reaction solution was added water, which was concentrated to dryness under reduced pressure. To the concentrate was further added water, which was concentrated under reduced pressure. To the concentrate (ca. 50 ml) was added acetic acid (2 ml), and the mixture was washed with ethyl acetate. The aqueous layer was concentrated under reduced pressure, then the organic solvent was distilled off. To the residue was added water again to make the whole volume 50 ml. To this aqueous solution was added platinum dioxide (200 mg), which was stirred at room temperature for 4 hours in a stream of hydrogen. The catalyst was filtered off, and the catalyst was washed with water. The filtrate and the washings were combined and concentrated to dryness under reduced pressure. The concentrate was subjected to an Amberlite CG-50 (NH$_4^+$) (180 ml) column chromatography. The column was washed with water (300 ml), followed by elution with 0.05N ammonia water. Fractions (1330–1880 ml) were combined and concentrated under reduced pressure, followed by freeze-drying to give valiolamine as a white powder (69 mg).

EXAMPLE 6

(1S)-(1(OH),2,4,5/1,3)-2,3,4-Tri-O-benzyl-5-[[2-hydroxy-1-(hydroxymethyl)ethyl]amino]-1-C-(benzyloxymethyl)-1,2,3,4-cyclohexanetetrol (1S)-(1(OH)),2,4/1,3)-2,3,4-Tri-O-benzyl-1-C-(benzyloxymethyl)-5-oxo-1,2,3,4-cyclohexanetetrol (600 mg) and 2-amino-1,3-propanediol (230 mg) were dissolved in methanol (40 ml), and then stirred 24 hours at room temperature. Sodium borohydride (1.0 g) was added to the mixture with cooling (ice-water bath), and then stirred 16 hours with cooling (ice-water bath). The mixture was concentrated in vacuo and the residue was partitioned between ethyl acetate (140 ml) and water (50 ml). The ethyl acetate layer was washed with water, dried with andhydrous sodium sulfate, and then evaporated in vacuo. The residue was chromatographed on a column of silica gel (60 ml) with ethyl acetate. The eluate was concentrated to dryness in vacuo to give (1s)-(1(OH),2,4,5/1,3)-2,3,4-tri-O-benzyl-5-[[2-hydroxy-1-(hydroxymethyl)ethyl]amino]-1-C-(benzyloxymethyl)-1,2,3,4-cyclohexanetetrol (380 mg) as a white powder: [α]$_D^{22}$ +30.0° (c=1, CHCl$_3$).

Elemental Analysis for C$_{38}$H$_{45}$NO$_7$: Calcd. (%): C, 72.70; H, 7.23; N, 2.23, Found (%): C, 72.43; H, 7.27; N, 2.31.

EXAMPLE 7

(1S)-(1(OH),2,4,5/1,3)-5-[[2-Hydroxy-1-(hydroxymethyl)ethyl]amino]-1-C-(hydroxymethyl)-1,2,3,4-cyclohexanetetrol (1S)-(1(OH),2,4,5/1,3)-2,3,4-Tri-O-benzyl-5-[[2-hydroxy-1-(hydroxymethyl)ethyl]amino]-1-C-(benzyloxymethyl)-1,2,3,4-cyclohexanetetrol (200 mg) was dissolved in 90% formic acid-methanol (1:19, 20 ml). Palladium black (100 mg) was added to the solution and the mixture was stirred overnight at room temperature in an atmosphere of nitrogen. The catalyst was filtered off and washed with methanol-water (1:1). The filtrate and the washings were combined and then evaporated in vacuo.

The residue was chromatographed on a column of Dowex 50 W×8 (OH⁻ type, 70 ml). The column was washed with water and eluted with 0.5N ammonium hydroxide, and the eluate was evaporated in vacuo. The residue was chromatographed on a column of Amberlite CG-50 (NH₄⁺ type, 180 ml) with water and the elute was evaporated to dryness in vacuo. Ethanol (10 ml) was added to the residue and then refluxed for 10 minutes. The mixture was refrigerated overnight to give (1S)-(1(OH),2,4,5/1,3)-5-[[2-hydroxy-1-(hydroxymethyl)ethyl]-amino]-1-C-(hydroxymethyl)1,2,3,4-cyclohexanetetrol (80 mg) as colorless crystals.

EXAMPLE 8

4L-4,6/5-Tri(benzyloxy)-3-(benzyloxymethyl)-2-cyclohexenone

To a solution of 3,4,5,7-tetra-O-benzyl-1-deoxy-1-(dimethoxyphosphoryl)-D-xylo-2,6-heptodiulose (12.5 g) in toluene (500 ml) were added 18-crown-6 (200 mg) and potassium carbonate (8.0 g). The mixture was stirred overnight at room temperature, and then insolubles were filtered off and washed with toluene. The filtrate and the wahings were combined, washed with 2N hydrochloric acid and saturated sodium hydrogencarbonate solution, dried over anhydrous sodium sulfate, and then concentrated under reduced pressure. The residue was chromatographed on a column of silica gel (500 ml) with toluene-ethyl acetate (20:1). The eluate was concentrated under reduced pressure and dried in vacuo to give 4L-4,6/5-tri(benzyloxy)-3-(benzyloxymethyl)-2-cyclohexenone (5.7 g).

$[\alpha]_D^{23} - 12.2°$ (c=1, CHCl₃), IR: $\nu_{max}^{CHCl_3}$ 1694 cm⁻¹ (C=O) ¹HNMR(CDCl₃) δ: 6.17–6.25 (1H, m, 2-CH).

Elemental Analysis for C₃₅H₃₄O₅: Calcd. (%): C, 78.63; H, 6.41, Found (%): C, 78.83; H, 6.27.

EXAMPLE 9

4L-4,6/5-Tri(tetrahydropyranyloxy)-3-(tetrahydropyranyloxymethyl)-2-cyclohexenenone (a) To a solution of 3,4,5,7-tetra-O-(tetrahydropyranyl)-1-deoxy-1-(dimethoxyphosphoryl)-D-xylo-2,6-heptodiulose (12.1 g) in toluene (500 ml) were added 18-crown-6 (200 mg) and potassium carbonate (8.0 g), and the mixture was stirred overnight at room temperature. Insolubles were filtered off and washed with toluene. The filtrate and the washings were combined, washed with 2N hydrochloric acid and saturated sodium hydrogencarbonate solution, dried over anhydrous sodium sulfate, and then concentrated under reduced pressure. The concentrate was chromatographed on a column of silica gel (500 ml) with toluene-ethyl acetate (3:1). The eluate was concentrated under reduced pressure and dried in vacuo to give 4L-4,6/5-tri(-tetrahydropyranyloxy)-3-(tetrahydropyranyloxymethyl)-2-cyclohexenone (7.5 g).

(b) To a solution of 3,4,5,7-tetra-O-(tetrahydropyranyl)-1-deoxy-1-(dimethoxyphosphoryl)-D-gluco-2-heptulopyranose (6.3 g) in toluene (50 ml) was added sodium hydride (270 mg). The mixture was stirred for two hours at room temperature, then insolubles were filtered off. On the other hand, a solution of trifluoroacetic anhydride (5.0 ml) in dichloromethane (25 ml) was added dropwise to a solution of dimethylsulfoxide (3.4 ml) in dichloromethane (25 ml) under cooling (−65° C. to −75° C.), and the mixture was stirred for 30 minutes. To the solution was added dropwise the above-mentioned toluene solution at the same temperature, and the mixture was stirred for one hour, to which was added dropwise a solution of triethylamine (10 ml) in dichloromethane (30 ml) at the same temperature. The mixture was stirred for 10 minutes, then the cooliing bath was removed. The mixture was allowed to warm to 0° C. with stirring. The reaction mixture was added to an ice-cooled mixture of dichloromethane (200 ml) and water (100 ml). The dichloromethane layer was separated, washed with water, dried over anhydrous sodium sulfate and concentrated under reduced pressure. The residue was dissolved in toluene (70 ml), to which were added 18-crown-6 (100 mg) and potassium carbonate (2.0 g). The mixture was stirred for 8 hours at room temperature. To the reaction mixture were added ethyl acetate (150 ml) and water (50 ml). The organic layer was separated, washed with 2N hydrochloric acid and saturated solution of sodium hydrogencarbonate, dried over anhydrous sodium sulfate and concetrated under reduced pressure. The concentrate was chromatographed on a column of silica gel (200 ml) with toluene-ethyl acetate (4:1). The eluate was concentrated under reduced pressure and dried in vacuo to give 4L-4,6/5-tri(tetrahydropyranyloxy)-3-(tetrahydropyranyloxymethyl)-2-cyclohexenone (1.3 g).

$[\alpha]_D^{26} + 2.3°$ (c=1, CHCl₃), IR: $\nu_{max}^{CHCl_3}$ 1690 cm⁻¹ (C=O). ¹HNMR(CDCl₃) δ: 6.14–6.25(1H, m, 2-CH)

Elemental Analysis for C₂₇H₄₂O₉: Calcd. (%): C, 63.51; H, 8.29, Found (%): C, 63.94; H, 8.36.

EXAMPLE 10

1L-(1,3/2,4)-2,3,4-Tri-O-benzyl-5-(benzyloxymethyl)-5-cyclohexene-1,2,3,4-tetrol To a solution of 4L-4,6/5-tri(benzyloxy)-3-(benzyloxymethyl)-2-cyclohexenone (2,7 g) in tetrahydrofuran-methanol (3:8, 55 ml) was added dropwise sodium borohydride (270 mg) at −20° C. The mixture was stirred for one hour at −15° C. to −20° C. The reaction solution was concentrated under reduced pressure, and the concentrate was distributed between ethyl acetate and water. The ethyl acetate layer was washed with 2N hydrochloric acid and saturated sodium hydrogencarbonate solution, dried over anhydrous sodium sulfate, and then concentrated under reduced pressure. The residue was chromatographed on a column of silica gel (180 ml) with toluene-ethyl acetate (7:1). The eluate was concentrated under reduced pressure and dried in vacuo to give 1L-(1,3/2,4)-2,3,4-tri-O-benzyl-5-(benzyloxymethyl)-5-cyclohexene-1,2,3,4-tetrol (2.6 g).

$[\alpha]_D^{26} - 30.9°$ (c=1, CHCl₃), ¹HNMR(CDCl₃) δ: 2.35(1H, s, -OH), 5.90 (1H, broad d, J=5 Hz, 6-CH).

Elemental Analysis for C₃₅H₃₆O₅: Calcd. (%): C, 78.33; H, 6.76, Found (%): C, 78.62; H, 6.74.

EXAMPLE 11

1L-(1,3/2,4)-2,3,4-Tri-O-tetrahydropyranyl-5-(tetrahydropyranyloxymethyl)-5-cyclohexane-1,2,3,4-tetrol To a solution of 4L-4,6/5-tri(tetrahydropyranyloxy)-3-(tetrahydropyranyloxymethyl)-2-cyclohexenone (25 g) in methanol (250 ml) was added sodium borohydride (2.5 g) at −10° C. to −15° C., and the mixture was stirred for 2.5 hours at the same temperature. The reaction solution was concentrated under reduced pressure, and the concentrate was partitioned between ethyl acetate (1 l) and 15% (W/V) sodium chloride solution (500 ml). The aqueous layer was extracted with ethyl acetate (500 ml). Ethyl acetate layers were combined, washed with saturated sodium chloride solution, dried over anhydrous sodium sulfate, followed by concentration under reduced pressure. The residue was chromatographed on a column of silica gel (1.1 l). The column was washed with toluene-ethyl acetate (2:1) and then eluted with toluene-ethyl acetate (3:2). The eluate was concentrated under reduced pressure and dried in vacuo to give 1L-(1,3/2,4)-2,3,4-tri-O-tetrahydropyranyl)-5-(tetrahydropyranyloxymethyl)-5-cyclohexene-1,2,3,4-tetrol (13.6 g).

$[\alpha]_D^{25} +2.9°$ (c=1, CHCl$_3$).

Elemental Analysis for C$_{27}$H$_{44}$O$_9$: Calcd. (%): C, 63.26; H, 8.65, Found (%): C, 63.67; H, 8.63.

EXAMPLE 12

1L-(1,3/2,4)-2,3,4-Tri-O-benzyl-1-O-(imidazolylsulfonyl)-5-(benzyloxymethyl)-5-cyclohexene-1,2,3,4-tetrol To a solution of 1L-(1,3/2,4)-2,3,4-tri-O-benzyl-5-(benzyloxymethyl)-5-cyclohexene-1,2,3,4-tetrol (2.5 g) in DMF (20 ml) was added dropwise sulfuryl chloride (0.79 ml) at −60° C., and the mixture was then stirred for 30 minutes at −40° C. to −45° C. The reaction solution was again cooled to −60° C., to which was added imidazole (3.3 g), followed by stirring for one hour at −10° C. The reaction mixture was added to an ice-cooled mixture of ethyl acetate (100 ml) and water (100 ml). The ethyl acetate layer was separated, and the aqueous layer was extracted with ethyl acetate (50 ml). The extract solutions were combined and washed with 2N hydrochloric acid and saturated sodium hydrogencarbonate solution, then dried over anhydrous sodium sulfate, followed by concentration under reduced pressure. The residue was chromatographed on a column of silica gel (150 ml) with toluene-ethyl acetate (20:1). The eluate was concentrated under reduced pressure and dried in vacuo to give 1L-(1,3/2,4)-2,3,4-tri-O-benzyl-1-O-(imidazolylsulfonyl)-5-(benzyloxymethyl)-5-cyclohexene-1,2,3,4-tetrol (1.6 g), $[\alpha]_D^{26} -16.7°$ (c=1, CHCl$_3$).

Elemental Analysis for C$_{38}$H$_{38}$N$_2$O$_7$S: Calcd. (%): C, 68.45; H, 5.47; N, 4.20; S, 4.81 Found (%): C, 68.92; H, 5.93; N, 3.99; S, 4.98.

EXAMPLE 13

1L-(1,3/2,4)-1-O-(Imidazolylsulfonyl)-2,3,4-tri-O-(tetrahydropyranyl)-5-(tetrahydropyranyloxymethyl)-5-cyclohexene-1,2,3,4-tetrol To a solution of 1L-(1,3/2,4)-2,3,4-tri-O-(tetrahydropyranyl)-5-(tetrahydropyranyloxymethyl)-5-cyclohexene-1,2,3,4-tetrol (11.3 g) in DMF (100 ml) was added dropwise sulfuryl chloride (4.3 ml) at a temperature of below −60° C., and the mixture was stirred for 30 minutes at −40° to −45° C. The reaction solution was again cooled to −60° C. or below, to which was added imidazole (14.55 g). The mixture was stirred overnight at 0°-5° C., followed by stirring for 3 hours at room temperature. The reaction mixture was added to an ice-cooled mixture of ethyl acetate (1 l) and water (250 ml). The ethyl acetate layer was separated, washed with water, dried over anhydrous sodium sulfate and concentrated under reduced pressure. The residue was chromatographed on a column of silica gel (550 ml) with toluene-ethyl acetate (5:1). The eluate was concentrated under reduced pressure and dried in vacuo to give 1L-(1,3/2,4)-1-O-(imidazolylsulfonyl)-2,3,4-tri-O-(tetrahydropyranyl)-5-(tetrahydropyranyloxymethyl)-5-cyclohexene-1,2,3,4-tetrol (8.5 g).

$[\alpha]_D^{24} -9.0°$ (c=1, CHCl$_3$).

Elemental Analysis for C$_{30}$H$_{46}$N$_2$O$_{11}$S: Calcd. (%): C, 56.06; H, 7.21; N, 4.36; S, 4.99, Found (%): C, 55.89; H, 7.34; N, 4.18; S, 5.33.

EXAMPLE 14

1L-(1,3/2,4)-1-O-(Methanesulfonyl)-2,3,4-tri-O-(tetrahydropyranyl)-5-(tetrahydropyranyloxymethyl)-5-cyclohexene-1,2,3,4-tetrol To a solution of 1L-(1,3/2,4)-2,3,4-tri-O-(tetrahydropyranyl)-5-(tetrahydropyranyloxymethyl)-5-cyclohexene-1,2,3,4-tetrol (2.55 g) in pyridine (20 ml) was added dropwise methanesulfonyl chloride (0.77 ml) at −20° C. to −30° C., and the mixture was then stirred at 0°-5° C. overnight. The reaction solution was concentrated under reduced pressure, and the residue was distributed between ethyl acetate and water. The ethyl acetate layer was washed with 2N hydrochloric acid and saturated sodium hydrogencarbonate soltuion, dried over anhydrous sodium sulfate, followed by concentration under reduced pressure. The residue was chromatographed on a column of silica gel (250 ml) with toluene-ethyl acetate (4:1). The eluate was concentrated under reduced pressure and dried in vacuo to give 1L-(1,3/2,4)-1-O-(methanesulfonyl)-2,3,4-tri-O-(tetrahydroxypyranyl)-5-(tetrahydropyranyloxymethyl)-5-cyclohexene-1,2,3,4-tetrol (1.21 g).

EXAMPLE 15

1D-(1,3,6/2)-1,2,3-Tri-O-(tetrahydropyranyl)-6-azido-4-(tetrahydropyranyloxymethyl)-4-cyclohexene-1,2,3-triol To a solution of 1L-(1,3/2,4)-1-O-(imidazolylsulfonyl)-2,3,4-tri-O-tetrahydropyranyl-5-(tetrahydropyranyloxymethyl)-5-cyclohexne-1,2,3,4-tetrol (1.7 g) in toluene (35 ml) was added tetra-n-butylammonium azide (1.7 g), and the mixture was stirred for 2 hours under reflux. To the reaction solution was added ethyl acetate (100 ml). The mixture was washed with water, dried over anhydrous sodium sulfate, followed by concentration under reduced pressure. The residue was chromatographed on a column of silica gel (150 ml) with toluene-ethyl acetate (4:1). The eluate was concentrated under reduced pressure and dried in vacuo to give 1D-(1,3,6/2)-1,2,3-tri-O-(tetrahydropyranyl)-6-azido-4-(tetrahydropyranyloxymethyl)-4-cyclohexene-1,2,3-triol (880 mg).

$[\alpha]_D^{24} +62.6°$ (c=1, CHCl$_3$), IR: $\nu_{max}^{neat}$ 2100 cm$^{-1}$ (azido) HNMR(CDCl$_3$) δ:5.81(1H, broad s, 5-CH).

Elemental Analysis for C$_{27}$H$_{43}$N$_3$O$_8$: Calcd. (%): C, 60.32; H, 8.06; N, 7.82, Found (%): C, 60.78; H, 8.32; N, 7.59.

EXAMPLE 16

1D-(1,3,6/2)-1,2,3-Tri-O-(tetrahydropyranyl)-6-azido-4-(tetrahydropyranyloxymethyl)-4-cyclohexene-1,2,3-triol To a solution of 1L-(1,3/2,4)-1-O-(methanesulfonyl)-2,3,4-tri-O-(tetrahydropyranyl)-5-(tetrahydropyranyloxymethyl)-5-cyclohexene-1,2,3,4-tetrol (1.1 g) in DMF (20 ml) was added sodium azide (250 mg), and the mixture was stirred for 3 hours at 80° C. The reaction mixture was concentrated under reduced pressure, and the concentrate was distributed between ethyl acetate and water. The ethyl acetate layer was washed with water, dried over anhydrous sodium sulfate, followed by concentration under reduced pressure. The residue was chromatographed on a column of silica gel (100 ml) with toluene-ethyl acetate (4:1). The eluate was concentrated under reduced pressure and dried in vacuo to give 1D-(1,3,6/2)-1,2,3-tri-O-(tetrahydropyranyl)-6-azido-4-(tetrahydropyranyloxymethyl)-4-cyclohexene-1,2,3-triol (1.0 g).

EXAMPLE 17

1D-(1,3,6/2)-Tri-O-(tetrahydropyranyl)-6-amino-4-(tetrahydropyranyloxymethyl)-4-cyclohexene-1,2,3-triol[-tetra-O-(tetrahydropyranyl)valienamine]

In tetrahydrofuran (47 ml) was dissolved 1D-(1,3,6/2)-1,2,3-tri-O-(tetrahydropyranyl)-6-azido-5-(tetrahydropyranyloxymethyl)-4-cyclohexene-1,2,3-triol (880 mg). To the solution was added by portions lithium aluminium hydride (280 mg) under cooling with ice-water, followed by stirring for 30 minutes at the same temperature then for 1.5 hour at room temperature. The reaction mixture was cooled with ice-water, to which was added dropwise methanol (ca. 10 ml) and then water (ca. 10 ml). The resultant insolubles were filtered off and washed with methanol. The filtrate and the washings were combined and concentrated under reduced pressure. The concentrate was distributed between ethyl acetate and water. The ethyl acetate layer was washed with water, dried over anhydrous sodium sulfate, then concentrated under reduced pressure, followed by drying in vacuo to give tetra-O-tetrahydropyranyl)valienamine (700 mg ).

EXAMPLE 18

1D-(1,3,6/2)-6-Amino-4-(hydroxymethyl)-4-cyclohexene-1,2,3-triol [valienamine]

A solution of tetra-O-(tetrahydropyranyl)valienamine (700 mg) in 80% acetic acid (35 ml) was stirred for 5 hours at 50° C. The reaction solution was concentrated under reduced pressure. The residue was chromatographed on a column of Dowex 50W×8 (H+ type, 130 ml). The column was washed with water, followed by elution with 0.5N ammonium hydroxide. The eluate was concentrated under reduced pressure. The concentrate was chromatographed on a column of Dowel 1×2 (OH⁻ type, 180 ml) with water. The eluate was concentrated under reduced pressure, followed by lyophilization to give valienamine (180 mg).

$[\alpha]_D^{24}$+87.6° (c=1, H$_2$O) $^1$HNMR (D$_2$O) δ: 5.89(1H, dd, J=1.5, 4.5 Hz, 5-CH), $^{13}$CNMR(D$_2$O+DCl): 50.2(d), 61.9(t), 67.4(d), 71.7(d), 72.5(d), 116.3(d), 146.5(s).

Elemental Analysis for C$_7$H$_{13}$NO$_4$.H$_2$O: Calcd. (%): C, 43.52; H, 7.83; N, 7.25, Found (%): C, 43.67; H, 7.82N, 7.28.

We claim:

1. An inosose compound of the formula

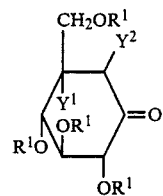

wherein $Y^1$ stands for hydroxyl group and $Y^2$ stands for hydrogen atom, or $CY^1CY^2$ is $C=C$, and $R^1$ is a protective group for hydroxyl group.

2. An inosose compound according to claim 1, wherein the compound is

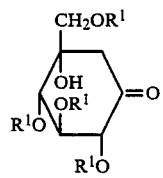

whose $R^1$ stands for a protective group for hydroxyl group.

3. An inosose compound according to claim 1, wherein the compound is

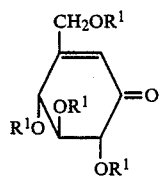

wherein $R^1$ stands for a protective group for hydroxyl group.

4. A method of preparing an inosose compound representable by the formula

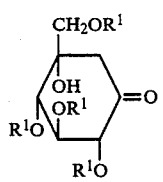

wherein $R^1$ stands for a protective group for hydroxyl group which comprises treating a compound representable by the formula

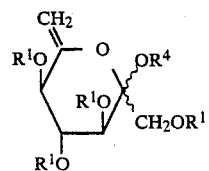

wherein $R^1$ is defined as above and $R^4$ is hydrogen or a protective group of the anomeric hydroxyl group, with a mercury (II) salt.

5. A method of preparing an inosose compound representable by the formula

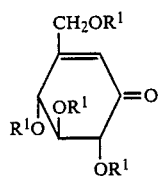

wherein $R^1$ stands for a protective group for hydroxyl group which comprises treating a compound representable by the formula

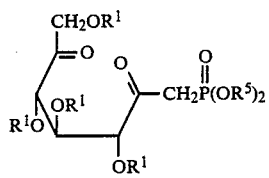

wherein $R^1$ stands for a protective group for hydroxyl group and $R^5$ stands for a hydrocarbon residue with a base.

6. A method of preparing a pseudoamino sugar of the formula

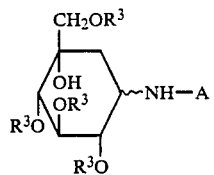

wherein $R^3$ stands for hydrogen atom or a protective group for hydroxyl group, A stands for an amine residue or hydrogen atom, and the wavy bond ∼∼ designates R- or S-configurational bond, which comprises allowing a compound of the formula

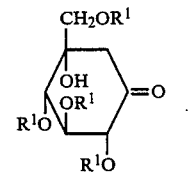

wherein $R^1$ stands for a protective group for hydroxyl group to react with a primary amine or hydroxylamine representable by the formula $R^2$-$NH_2$, wherein $R^2$ stands for an amine residue or hydroxyl group, and then subjecting the resultant Schiff base product to reduction and, in the case when $R^3$ is hydrogen, removal of the protective group.

7. Compound of claim 2, wherein $R^1$ is benzyl.

* * * * *